United States Patent
Buck

(10) Patent No.: US 10,828,108 B2
(45) Date of Patent: Nov. 10, 2020

(54) ORTHOPAEDIC OR BIOLOGIC SUPPORT STRUCTURE, METHODS OF MAKING AND METHODS OF USE

(71) Applicant: Buck Medical Research LTD., Rowlett, TX (US)

(72) Inventor: Monty B. Buck, Rowlett, TX (US)

(73) Assignee: Buck Medical Research Ltd., Rowlett, TX (US)

(*) Notice: Subject to any disclaimer, the term of this patent is extended or adjusted under 35 U.S.C. 154(b) by 195 days.

(21) Appl. No.: 15/739,685

(22) PCT Filed: Jun. 23, 2016

(86) PCT No.: PCT/US2016/039106
§ 371 (c)(1),
(2) Date: Dec. 22, 2017

(87) PCT Pub. No.: WO2016/210184
PCT Pub. Date: Dec. 29, 2016

(65) Prior Publication Data
US 2018/0185098 A1    Jul. 5, 2018

Related U.S. Application Data

(60) Provisional application No. 62/184,578, filed on Jun. 25, 2015, provisional application No. 62/241,118, filed on Oct. 13, 2015.

(51) Int. Cl.
*A61B 34/10* (2016.01)
*A61B 17/00* (2006.01)
(Continued)

(52) U.S. Cl.
CPC .......... *A61B 34/10* (2016.02); *A61B 17/00491* (2013.01); *A61B 17/58* (2013.01);
(Continued)

(58) Field of Classification Search
CPC .......... B33Y 80/00; B33Y 70/00; B33Y 50/00; B33Y 10/00; A61B 17/00491;
(Continued)

(56) References Cited

U.S. PATENT DOCUMENTS 7,029,275 B2   4/2006  Rubbert et al.
8,485,820 B1   7/2013  Ali
(Continued)

FOREIGN PATENT DOCUMENTS

| WO | WO 2007045000 | 4/2007 | |
|---|---|---|---|
| WO | WO-2007045000 A2 * | 4/2007 | ......... A61B 17/8061 |
| WO | WO 2016210184 | 12/2016 | |

OTHER PUBLICATIONS

Notification of Transmittal of the International Search Report and the Written Opinion of the International Searching Authority, or the Declaration, International Search Report, and Written Opinion of the International Searching Authority, for PCT/US2016/039106, dated Oct. 25, 2016, 14 pages.
(Continued)

*Primary Examiner* — Christine H Matthews
*Assistant Examiner* — Joshua Daryl D Lannu
(74) *Attorney, Agent, or Firm* — Monique A. Vander Molen

(57) ABSTRACT

A support for use with tissue or bone is described, the support having one or more spaced apart brace members, and at least one elongated linking member for linking to the one or more spaced apart brace members. The support may be provided in use in combination with a biologic glue, the biologic glue comprising a first portion containing stabilized blood product, and a second portion containing a growth factor, the first portion and the second portion comingled when or after the support is introduced to the tissue or bone in a subject in need thereof. The support is fabricated by
(Continued)

actively producing the support through an additive manufacturing process, in which the support is customized specifically to the tissue or bone by creating a computer-generated construct of the support on a three-dimensional volume rendering of the tissue or bone, and the computer generated construct is interpretable via software directing the additive manufacturing process.

20 Claims, 9 Drawing Sheets

(51) Int. Cl.
*A61F 2/00* (2006.01)
*A61L 27/36* (2006.01)
*A61L 27/54* (2006.01)
*A61L 27/56* (2006.01)
*B33Y 10/00* (2015.01)
*B33Y 80/00* (2015.01)
*B33Y 70/00* (2020.01)
*B33Y 50/00* (2015.01)
*B29C 67/00* (2017.01)
*A61F 5/01* (2006.01)
*A61B 17/58* (2006.01)
*A61C 8/00* (2006.01)
*A61C 13/00* (2006.01)
*A61B 17/56* (2006.01)
*A61B 17/68* (2006.01)
*B22F 3/105* (2006.01)

(52) U.S. Cl.
CPC .......... *A61C 8/0031* (2013.01); *A61C 8/0095* (2013.01); *A61C 13/0004* (2013.01); *A61C 13/0013* (2013.01); *A61F 2/0059* (2013.01); *A61F 5/01* (2013.01); *A61L 27/3616* (2013.01); *A61L 27/54* (2013.01); *A61L 27/56* (2013.01); *B29C 67/00* (2013.01); *B33Y 10/00* (2014.12); *B33Y 50/00* (2014.12); *B33Y 70/00* (2014.12); *B33Y 80/00* (2014.12); *A61B 2017/00526* (2013.01); *A61B 2017/00893* (2013.01); *A61B 2017/561* (2013.01); *A61B 2017/568* (2013.01); *A61B 2017/681* (2013.01); *A61B 2034/102* (2016.02); *A61B 2034/108* (2016.02); *A61C 8/0048* (2013.01); *A61F 2002/0086* (2013.01); *A61F 2240/002* (2013.01); *A61L 2300/414* (2013.01); *B22F 3/1055* (2013.01)

(58) Field of Classification Search
CPC .............. A61B 17/58; A61B 2017/568; A61B 2034/108; A61B 2034/102; A61B 34/10; A61B 2017/681; A61B 2017/561; A61B 2017/00893; A61B 2017/00526; B29C 67/00; A61C 8/0031; A61C 8/0048; A61C 8/0095; A61C 13/0004; A61C 13/0013; A61L 2300/414; A61L 27/56; A61L 27/3616; A61L 27/54; B22F 3/1055; A61F 2240/002; A61F 2002/0086; A61F 2/0059; A61F 5/01
See application file for complete search history.

(56) References Cited

U.S. PATENT DOCUMENTS

| 8,491,564 | B2 | 7/2013 | Beretta et al. |
| 8,888,485 | B2 | 11/2014 | Ali |
| 2004/0219182 | A1 | 11/2004 | Gomes et al. |
| 2007/0118243 | A1 | 5/2007 | Schroeder et al. |
| 2010/0143868 | A1 | 6/2010 | Hintersehr |
| 2010/0291508 | A1 | 11/2010 | Jensen |
| 2010/0318121 | A1 | 12/2010 | Levin et al. |
| 2011/0288652 | A1 | 11/2011 | Kacena et al. |
| 2012/0165871 | A1 | 6/2012 | Malone |
| 2012/0310264 | A1 | 12/2012 | Messerly et al. |
| 2013/0310963 | A1 | 11/2013 | Davison |
| 2014/0010951 | A1 | 1/2014 | Vargas et al. |
| 2014/0180185 | A1 | 6/2014 | Zachariasen |
| 2015/0018888 | A1 | 1/2015 | Geebelen |
| 2015/0037756 | A1 | 2/2015 | Berckmans, III et al. |
| 2015/0093717 | A1 | 4/2015 | Ali |
| 2015/0165690 | A1 | 6/2015 | Tow |

OTHER PUBLICATIONS

Notification of Transmittal of International Preliminary Report on Patentability (IPRP), and IPRP, for PCT/US2016/039106, dated Jun. 3, 2017, 7 pages.

* cited by examiner

FIG. 7A
FIG. 7B
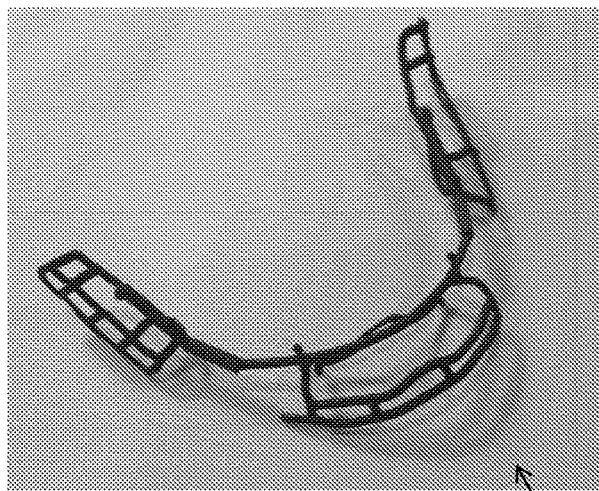
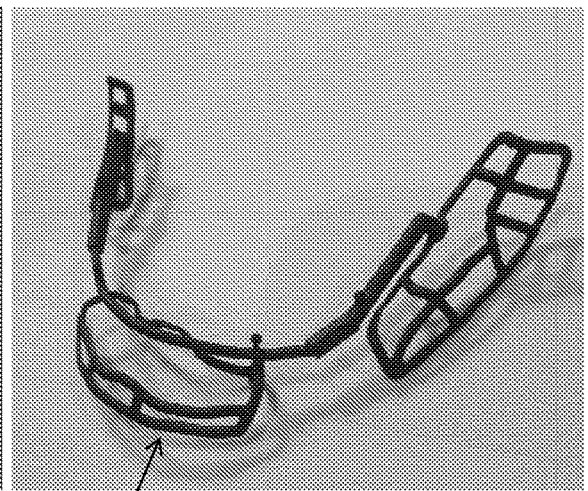
70

ORTHOPAEDIC OR BIOLOGIC SUPPORT STRUCTURE, METHODS OF MAKING AND METHODS OF USE

CROSS-REFERENCES TO RELATED APPLICATIONS

This application claims the benefit of priority to U.S. Provisional Application No. 62/184,578 filed Jun. 25, 2015, and U.S. Provisional Application No. 62/241,118 filed Oct. 13, 2015, each of which is incorporated herein in its entirety, and to the maximal extend allowable.

BACKGROUND

The invention as described herein relates to supports, support systems, methods of making and methods of use. Said supports and systems for use in vivo are highly customized and serve as orthopaedic or soft tissue supports and/or replacements for orthopaedic or soft tissue portions in need thereof.

Most current orthopaedic or tissue supports are off-the-shelf. Ones that are so-called customizable are generally made so by taking an off-the-shelf component and milling and/or adding additional feature, thereby introducing inefficiencies, added cost, and points of possible excess strain and/or stress (e.g., potential points of failure). Some so-called customized components require initial and/or post-process fittings and/or impressions made of the actual tissue, thereby requiring additional steps (e.g., debriding, degloving), introducing post-operative issues, inefficiencies and cost. Some so-called customized components are manufactured by extruding into a mold, in which the mold may be in a form that may provide a so-called customized product; however, the molding requires additional steps, and introduces inefficiencies and added cost.

There remains a need for support structures that are customized from inception and can include features when fabricated that reduce strain and/or stress (e.g., potential points of failure), are more accurate and replicate much of the original tissue architecture, require less overall damage when introduced to a tissue in need, which enhance healing and/or remodeling, and are prepared with more precision, fewer steps and cost less.

SUMMARY

Described herein are support members, support systems and method of making. The support member is customized for a particular bone or tissue region and will include contact regions for contact with an adjacent bone or tissue. The method provides a customized support member that is customized and/or specifically designed for the particular bone or tissue region in need of the support member. The method identifies architecture at and/or neighboring the particular bone or tissue region and provides the customized support member with more accuracy, prepared with fewer steps and at less cost as compared with current bone or tissue implants.

In one or more embodiments is a method of fabricating a tissue device, the method comprising: obtaining a volumetric data set of at least a portion of a tissue (the at least a portion of the tissue being a tissue or portion thereof for which a tissue device is to be configured, and/or which is a tissue or portion thereof is to be treated, and the volumetric data set being obtained from a plurality of images of the portion of the tissue captured from the tissue or portion thereof, or from a tissue representative of the tissue or portion thereof); processing the volumetric data set and providing a three-dimensional rendition of the tissue, the three-dimensional rendition being associated with and/or accessible by a computing device comprising digital data; designing or painting a support construct on the three-dimensional rendition associated with the computing device; providing a data file of the designed or painted support construct, the data file associated with and/or accessible by the computing device, the painted support construct associated with or being a three-dimensional construct of a tissue device that is to be configured for the at least the portion of the tissue (e.g., the tissue for which the tissue device is configured for, and/or which is to be treated); utilizing the three-dimensional construct and slicing and/or otherwise processing the data file into data units or data fragments and/or consecutive thin data sections; and actively producing a three-dimensional support based on the data units or data fragments and/or consecutive thin data sections. The obtaining a volumetric data set of the tissue is acquired by one of computer tomography (e.g., cone beam computer tomography, CAT), magnetic resonance imaging, ultrasound, and the like. The obtaining the volumetric data set of the tissue is performed by acquiring images of the tissue and volume rendering data points from the images. The obtaining the volumetric data set of the tissue is performed by acquiring images of the tissue and including level set segmentation techniques. The obtaining the volumetric data set of the tissue is performed by acquiring images of the tissue and including level set segmentation techniques with automatic seed initialization and maximum intensity projection. The obtaining the volumetric data set of the tissue further comprises extrapolating from images obtained from a complimentary tissue to provide a subset of the volumetric data set. The obtaining the volumetric data set of the tissue further comprises extrapolating from prior images of the tissue to provide a subset of the volumetric data set. The painting the support construct includes creating computer generated images. The painting the support construct includes creating a texture map in a modeling program. The painted support construct includes one or more of a discontinuous network of spaced apart brace members, prosthetic attachments, webbing, and the like providing a loose, discontinuous network, a portion of which following in form and shape at least part of the architecture of the at least a portion of a tissue. The actively producing the three-dimensional support is performed by an additive manufacturing process utilizing a metal powder material in the additive manufacturing process. With the method, further construction of the three-dimensional support (e.g., active modifications, such as milling or welding) after actively producing the support utilizing an additive manufacturing process is not required; however the three-dimensional support may be sterilized before being utilized as a supportive and/or reconstructive and/or prosthetic device.

In further embodiments is a method of fabricating an orthopaedic support, the method comprising: obtaining a volumetric data set of a bone; providing a three-dimensional rendition of the bone; designing or painting a support construct on the three-dimensional rendition; providing a data file of the painted support construct; directly producing a three-dimensional support (via an additive manufacturing processing) based on the data file, without any other intermediate steps. The data file may comprise a three-dimensional virtual or digital design that is produced (e.g., painted and/or drawn) directly on the three-dimensional rendition (and/or on a scan).

In one or more embodiments the support member is a frame for an individual bone or tissue in need thereof. The support member may be an implant or prosthesis for an individual bone or tissue in need thereof. The support member may be replacement architecture for an individual bone or tissue in need thereof. The support member as described herein is completely customized from inception to mate with at least a portion of the bone or tissue to which it will be introduced. The support member will include features specific to the bone or tissue in need thereof. The support member may reduce stress and/or strain (e.g., potential points of failure) when introduced to the bone or tissue in need thereof. The support member will reduce overall damage to bone or tissue in need thereof when introduced. The support member itself, being customized for a tissue in need thereof, will require less invasive means to introduce the support member. Moreover, by customizing such a support member so that is meets some or all of the architectural requirement of the tissue in need, it ensures that the most amount of original tissue is retained by the subject or patient, rather than being removed, which is often the case in injuries that occur at joints, bone or certain other tissue.

In some embodiments, the support member fits and resides on some or all of the exposed surface of the bone or tissue region, thereby matingly and compatibly fitting with said surface so that it compatibly fits with the outer morphology (e.g., curves, etc.) of said bone or tissue region.

In some embodiments, the support member fits and resides on some or all of the exposed surface of the bone or tissue region and provides an artificial surface to define a portion of the bone or tissue region that has been damaged or is missing, thereby matingly and compatibly fitting with the existing surfaces to compatibly fit with the existing outer morphology (e.g., curves, etc.) of said bone or tissue region and also: (i) defining some or all of the outer morphology that was damaged, removed, or missing, in order to provide a region and boundary for new tissue growth; and/or (ii) providing a scaffold or template on which new tissue can grow. The tissue growth may be enhanced with the presence of a composition (filler material) as described herein below.

The described support member being customized and less invasive and/or requiring less surgical time to provide to a subject or patient in need should also time of enhance healing and/or the amount of modeling and/or growth and/or reconstruction and/or remodeling of the bone or tissue region in need thereof. The support member may also include the composition (filler material) as described herein below that further enhances healing and/or reconstruction and/or growth and/or remodeling of the bone or tissue region in need thereof to which it is introduced. The support member or structure described herein is cost-effective, reducing surgical time. The support member will reduce overall time involved from initial preparation to fabrication to introduction to the bone or tissue in need thereof.

The support member will generally include one or more contact points adjacent to or in contact with the individual bone or portions of the individual bone. The support system includes the support member and complementary components, such as complementary hardware device.

The support member may serve as a frame. For example, the support member may serve as a frame for holding and maintaining two portions of bone or other tissue in need thereof while the bone or tissue undergoes repair and remodeling. In addition, or as an alternative, the support member may serve as a frame for attaching another component in position with respect to the bone or tissue in need thereof.

The support member, the support system and methods of use of said support member and support systems as described herein may be suitable for any tissue, including bone.

In one or more embodiments is a tissue device having one or more spaced apart brace members and at least one elongated linking member for linking to the one or more spaced apart brace members. The orthopaedic support may further comprise one or more projections. The orthopaedic support may further comprise one or more bore holes. The one or more spaced apart brace members include a plurality of stress-distributing elements, each spaced apart forming gaps there between. The one or more spaced apart brace members may form a networked arrangement that is not one continuous solid structure. The plurality of stress-distributing elements forming each of the one or more spaced apart brace members is solid. The plurality of stress-distributing elements forming each of the one or more spaced apart brace members has an open center. The plurality of stress-distributing elements forming each of the one or more spaced apart brace members are porous. The one or more spaced apart brace members form a configuration that is complementary to a surface of bone to which it is to be in contact with. The one or more spaced apart brace members include bone contacting surface and non-bone contacting surfaces. The at least one elongated linking member is not for contacting bone when the orthopaedic support is positioned on or within the bone.

Also described is a tissue device having one or more spaced apart brace members and at least one elongated linking member for linking to the one or more spaced apart brace members, the orthopaedic support provided in use in combination with a biologic glue, the biologic glue comprising a first portion containing a stabilized blood product (e.g., autogenous platelet rich plasma, platelet rich fibrin), and a second portion containing a bone specific morphogenetic factor, the first portion and the second portion comingled only when the orthopaedic support is introduced to a subject or patient in need thereof. The first portion further comprises a supplemental agent. The stabilized blood product may be autogenous platelet rich plasma comprising concentrated autologous blood that includes autogenous platelets, stem cells, growth factor, and cytokines from the blood used to form the platelet rich plasma. The stabilized blood product may be autogenous platelet rich fibrin comprising concentrated autologous blood (centrifuged blood comprising platelets, leucocytes, cytokines, circulating stein cells) and a fibrin mixture or membrane. The second portion further comprises calcium chloride and thrombin. The morphogenetic factor may be, for example, human recombinant bone morphogenetic protein 2.

In addition, described herein is a system comprising an orthopaedic or tissue support and a biologic glue, the orthopaedic support having one or more spaced apart brace members and at least one elongated linking member for linking to the one or more spaced apart brace members. The biologic glue comprises a first portion containing a stabilized blood product (e.g., autogenous platelet rich plasma, platelet rich fibrin), and a second portion containing a bone specific morphogenetic factor, the first portion and the second portion separable until use of the orthopaedic support.

In one or more embodiments is an orthopaedic or tissue support having one or more spaced apart brace members and at least one elongated linking member for linking the one or more spaced apart brace members. The support may further comprise one or more projections extending outwardly from a facing surface of the tissue for which the support is configured for. At least a portion of the support will have an architectural shape matching at least a portion of the facing surface or which the support is configured for. The support may further comprise one or more bore holes. The one or more spaced apart brace members include a plurality of stress-distributing elements, each spaced apart forming gaps there between. The one or more spaced apart brace members may form a networked arrangement that is not one continuous solid structure. The plurality of stress-distributing elements forming each of the one or more spaced apart brace members is solid. The plurality of stress-distributing elements forming each of the one or more spaced apart brace members has an open center. The plurality of stress-distributing elements forming each of the one or more spaced apart brace members for a network. The one or more spaced apart brace members form a configuration that is complementary to a surface to which the support is to be in contact with and/or adjacent to. The one or more spaced apart brace members include one or more tissue contacting surfaces, and non-tissue contacting surfaces. The at least one elongated linking member is not for contacting the tissue when the orthopaedic or tissue support is positioned on or within the tissue.

Also described is an orthopaedic or tissue support having one or more spaced apart brace members and at least one elongated linking member for linking to the one or more spaced apart brace members, the support provided in use in combination with a biologic glue, the biologic glue comprising a first portion containing stabilized blood product (e.g., autogenous platelet rich plasma, platelet rich fibrin), and a second portion containing a tissue specific morphogenetic factor, the first portion and the second portion comingled only when the support is introduced to a subject or patient in need thereof. The first portion further comprises a supplemental agent. The stabilized blood product may comprise autogenous platelet rich plasma, or autogenous platelet rich fibrin. The second portion further comprises calcium chloride and thrombin. The morphogenetic factor may be carried by and/or may be topographically stabilized by the stabilized blood product, and may include, for example, human recombinant morphogenetic protein 2.

Further described is a system comprising an orthopaedic or tissue support support, and a biologic glue, the support having one or more spaced apart brace members, and at least one elongated linking member for linking to the one or more spaced apart brace members. The biologic glue comprises at least a stabilized blood product (e.g., autogenous platelet rich plasma, platelet rich fibrin), and a tissue specific morphogenetic factor, which are kept separate until utilized with the support.

These and other embodiments are further described below.

BRIEF DESCRIPTION OF THE DRAWINGS

For a more complete understanding of various embodiments of the present disclosure and the advantages thereof, reference is now made to the following brief description, taken in connection with the accompanying drawings, appendices, and detailed description, wherein like reference numerals represent like parts, and in which:

FIGS. 7A and 7B illustrate two views of a representative example of a three-dimensional support member produced by the process as described herein.

DESCRIPTION OF THE VARIOUS REPRESENTATIVE EMBODIMENTS

Described herein is a three-dimensional support member, support system, methods of making said support member and/or system and methods of use. In one embodiment, the support member is specific for an individual bone or bone region. The bone or bone region may be weight bearing or non-weight bearing. The bone or bone region may be one requiring support and/or may be damaged (e.g., due to an injury, surgery, disease, and/or developmental anomaly, in which the injury, surgery, disease and/or anomaly occurred prior to requiring the support). In additional embodiments, the support member is specific for an individual tissue or physiologic region. The tissue or physiologic region may be weight bearing or non-weight bearing. The physiologic region may include bone. The tissue or physiologic region may be one requiring support and/or may be damaged (e.g., due to an injury, surgery, disease, and/or developmental anomaly, in which the injury, surgery, disease and/or anomaly occurred prior to requiring the support).

Figure 1A:
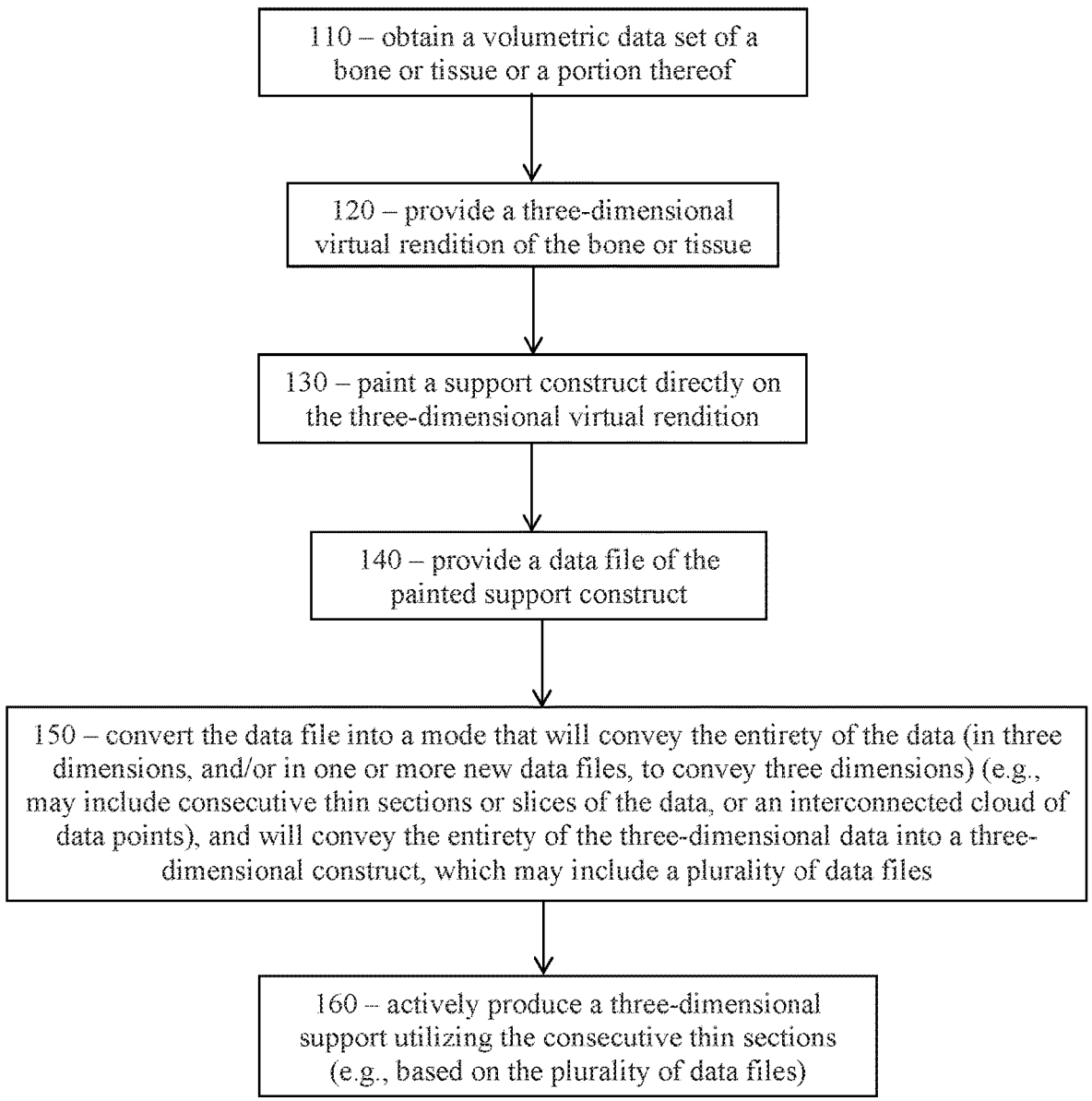
FIGS. 1A and 1B are representative schematics of methods described herein.
Figure 1B:
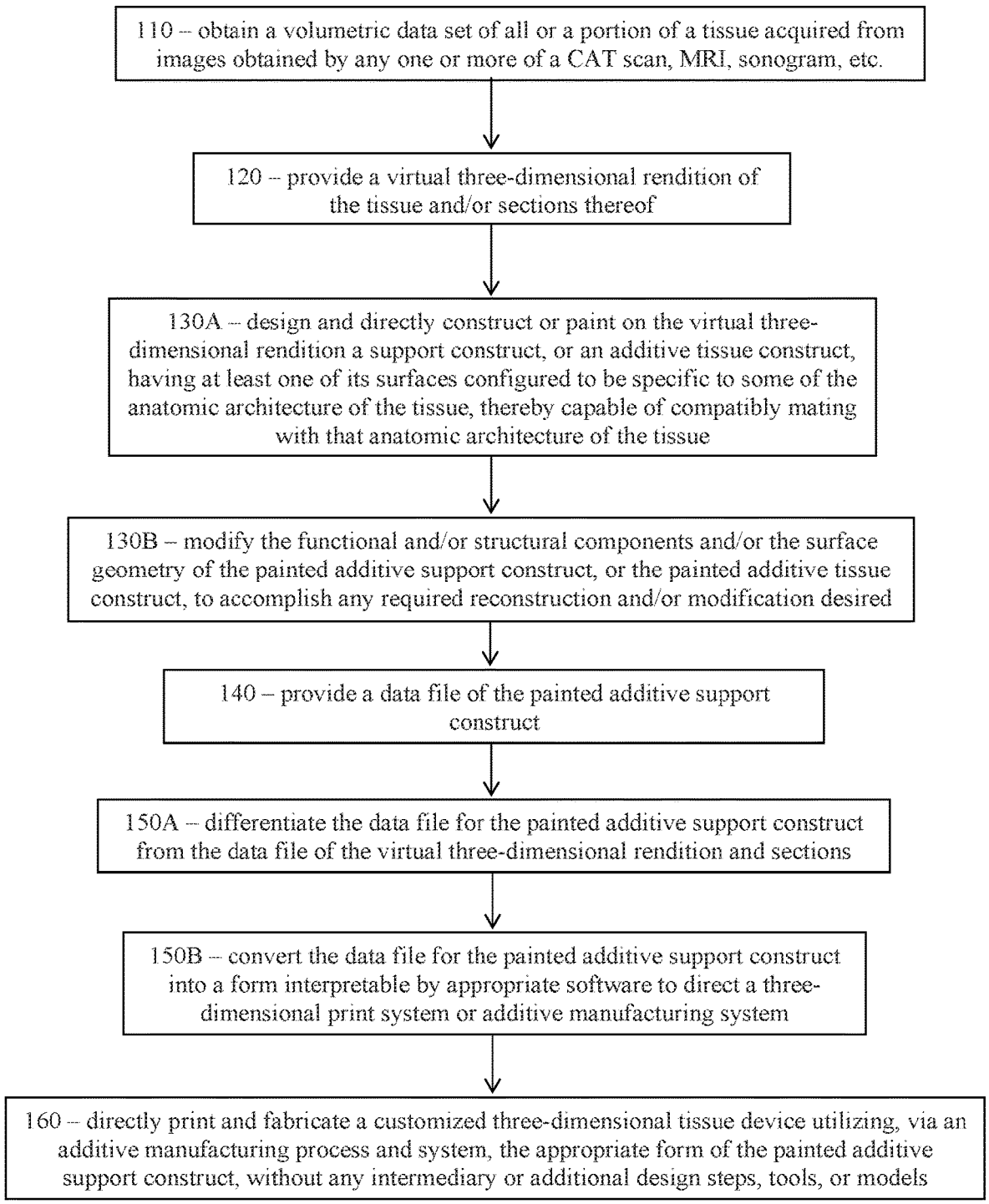

The individually customized support as described herein is provided by customized methods, represented in FIGS. 1A and 1B. In an initial phase 110 to 120, using bone, or a bone region as a representative tissue/physiologic region, a three-dimensional rendition 30 of a bone (or bone region) 5 is obtained noninvasively. This means there is no degloving or debriding required. The obtaining of the three-dimensional rendition includes obtaining a plurality of images, such that there is a volumetric data set 10 of the bone 5 (block 110). The volumetric data set 10 will at least include the bone region 5 for which the support will be configured for, and/or the whole bone containing the region 5 requiring support. The volumetric data set 10 will be processed and/or obtained from one or more or a set of images provided by an image capture device. When the bone or bone region 5 includes a loss of bone in the bone or bone region 5, the volumetric data set 10 may be or may be extrapolated from (or overlayed with) a prior image or set thereof of the uninjured or intact bone or bone region, or from an image or set thereof of an opposing bone (intact and uninjured) or of an intact and uninjured bone region (e.g., using a left bone for loss in a right bone), or from an image or set thereof of an age-related (and/or race-related and/or representative bone containing an intact bone or at least an intact same region of bone as bone region 5) as a non-injured bone or bone region. The image or set thereof may be an archived set of images. The image or set thereof may be images obtained from age-related (and/or race-related) cadaveric tissue (representative of the bone or bone region that contains an intact same region of bone) non-injured bone or bone region. Said representative image or set thereof (e.g., axial scan) and/or volumetric data (e.g., archived and/or cadaveric images and/or volumetric data about said archived and/or cadaveric images) may be stored in a database or memory device. The volumetric data set 10 is, in one some embodiments, obtained by utilizing an image capture device or system, such as tomography or other image capturing system 15, for example, a cone beam computed tomography device. Alternative tomography, such as helical computed tomography (CT), or other image capturing devices 15 may be used. For example, magnetic resonance imaging (MRI), or ultrasound (US), provide each image as a scan, or as sonogram, respectively. In one or more embodiments, cone beam computed tomography is utilized, and may, in some embodiments, be preferred, in which the volumetric data set 10 is obtained from data captured by a computed tomography scanner that works with divergent x-rays, utilized with or without contrast setting. In one or more embodiments, the volumetric data set 10 is acquired as three-dimensional data (e.g., three-dimensional CT with volume rendering, such as via axial CT sections integrated in series forming a three-dimensional rendering of volume elements, or voxels). Other rendering techniques may be provided, including shaded surface display, or surface rendering, maximum intensity projection, as examples. In alternative embodiments, magnetic resonance imaging, ultrasound, digital, or any suitable alternative imaging system with a corresponding scanning or image capture device is used to provide three-dimensional data. With any such imaging system, a scanning device and/or image capture device creates a plurality of image files (e.g., DICOM or similar type image files). The captured scans (e.g., image files) must provide clear tissue edges and fine details. Thus, a smallest field possible may be utilized. In some embodiments, a smallest field possible for an axial scan that encompasses the full region of bone 5 is preferred, where possible. In some embodiments, a scout view (digital radiograph) is obtained prior to obtaining axial CT sections. In one example, axial CT scans were obtained with the CT device set to 120 kV, with a pitch ≤1, matrix of 512×512, and a smallest possible field of view to encompass the entire area for which a support structure was to be configured for. In one example, for axial CT scans, the slice thickness was 0.50 mm to 1 mm, the slice increment was 0.625 to 0.75 (with 50% overlap), and kernel/algorithm was set to moderate for soft tissue (and was not set for bone detail). In one or more embodiments, there were no secondary or oblique reconstructions. In one or more embodiments, there was no reformatting of images.

Using available or customized software, the image files (or similar type files) are saved. Generally, only actual image files (scans as DICOM files) are utilized. Generally, none of the image files (or data thereof) are reconstructed image files, are not reformatted image files, and are not lossy compression files. In one or more embodiments, the files contain data in accordance with one or more of ISO/IEC 109018-1, ISO/IEC 14495-1, ISO/IEC 15444-1, ISO/IEC 13818-1. In one or more embodiments, the images are retained in accordance with PACS (picture archiving and communication system), as is understood in the art. In one or more embodiments, appropriate images (e.g., with or without subject/patient information, office information, and/or prescriber/physician information) are provided from a first computing device and/or system to a second computing device and/or system, in which the second computing device and/or system may be remote from the first. In some embodiments, the first computing device and/or system is, or is associated with, a medical facility. In some embodiments, the second computing device and/or system is, or is associated with, a manufacturing facility.

The image files are converted to provide a three-dimensional (3D) file 20 (e.g., stereolithography file, or .STL file) using available or customized software. The three-dimensional (3D) file 20 may be saved and/or utilized to provide a volumetric data set 10, and an accompanying three-dimensional rendition 30 of the bone or bone region 5 (block 120). The three-dimensional rendition 30 is a three-dimensional visual computer model of the bone 5. Software for providing the 3D file 20 and the three-dimensional rendition 30 used alone or in appropriate combinations, include but are not limited to Clara, InVesalius, OsirX, 3D slicer, ITKSnap, etc. Some or all of the plurality of image files may be stacked and used for segmentation prior to or when converting to the 3D file 20. These actions may be performed at any location having said software, and accompanying hardware (e.g., computing device with appropriate processors, control unit, operating system, storage, and the like for implementing one or more of the process actions or steps via computer-implemented media). When the plurality of image files are converted, the original or image files may, or may not, be converted from 32-bit to 16 bit precision or to 8 bit. Preferably, there is appropriate bit depth or precision in the conversion.

Figure 2A:
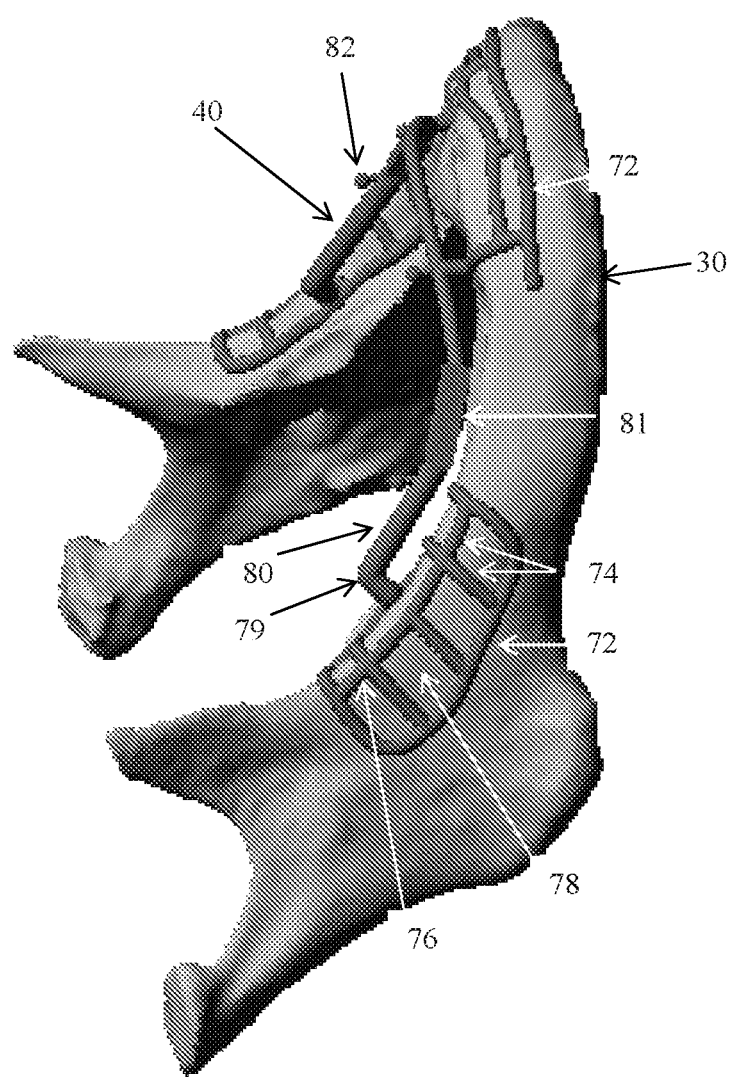
FIG. 2A is a representative schematic of a three-dimensional rendition and a painted construct as described herein.

In a next phase, depicted in FIGS. 1A and 1B as 130 and 140, a suitable support construct 40 is painted on the three-dimensional rendition 30 of the bone or bone region 5 (blocks 130, 130A, and/or 130B). Painting may be performed on the three-dimensional rendition 30 or on a mesh provided by or in combination with the three-dimensional rendition 30. An example of a painted support construct 40 on a three-dimensional rendition 30 of mandibular bone 5 is illustrated in FIG. 2A. The painted support construct 40 is provided as a separate data file 50 (block 140). The painted support construct 40 (or the one or more meshes created from the data file 50) may be further analyzed for stress/strains in a finite element modeling (FEM) system or simulation system or optimization system. In some embodiments, the separate data file 50 is an .STL file. Other file types are also acceptable. In some embodiments the separate data file 50 is used to generate one or more solid models and/or meshes for FEM analysis or for simulation or for optimization, utilizing corresponding software that performs one or more of an FEM analysis, simulation or optimization of the painted support construct 40 (provided by all or part of the separate data file 50). FEM analysis or simulation or optimization is performed as understood by those in the relevant art (e.g., generating surface models, solid models and/or meshes, creating boundaries, setting boundary conditions, introducing one or more loads or other simulated or optimization conditions). FEM analysis or simulation or optimization can help improve design of the painted support construct 40 (e.g., overall shape, size, number of required features, etc.) prior to making a final support member 70, in which the painted support construct 40 is the construct used to fabricate the final support member 70. FEM analysis or simulation or optimization can also help to improve design of the painted support construct 40 (e.g., overall, structure, number of required features, etc) after making the final support member 70. For example, the FEM analysis or simulation or optimization can model density, residual stress, mechanical behavior (surface or as a solid), nonequilibrium microstructures and their behaviors, and material properties based on the painted support construct 40 or the final support member 70, as representative examples. These actions may be performed at any location having said painting and modeling software, and accompanying hardware (e.g., computing device with appropriate processors, control unit, operating system, storage, and the like for implementing one or more of the process steps via computer-implemented media). Design (e.g., blocks 130, 130A, and/or 130B) may be performed by or in association with a physician. The design may be performed by a reconstructive biodesign technician associated with the physician or remote from the physician.

In a next phase, depicted in FIGS. 1A and 1B as 150, 150A, 150B and 160, the painted support construct 40 (e.g., containing data file 50) is used to actively produce a three-dimensional support member 70. In a prototyping process, the three-dimensional support member 70 is constructed utilizing a three-dimensional printing process, or additive manufacturing process. In some embodiments, the painted support construct 40 (e.g., via data in the data file 50) is differentiated from the data file of the three-dimensional rendition 30 and the file is prepared for the processing by appropriate software (blocks 150, 150A, and/or 150B). The painted support construct 40 may be initially sliced into a plurality of thin cross sectional layers 60. Each thin cross sectional layer 60 (e.g., data in the cross sectional layer 50) is utilized to construct a layer for the three-dimensional support member 70, and layer by layer, the three-dimensional support member 70 is fabricated (block 160). The prototyping process or additive manufacturing process may use one or more extrusion heads and/or nozzles to deposit a thin layer of material, one layer at a time (e.g., in which each thin layer corresponding to the thin cross sectional layer 60 of the painted support construct 40). In addition, or alternatively, a thin layer of material may be hardened, or cured, or sintered, or melted, or fused, generally one layer at a time (e.g., using a laser or electron beam or electromagnetic coils, as examples, to form the three-dimensional support member 70). Representative techniques include, but are not limited to, selective laser melting, direct metal laser sintering, electron beam melting, or laser fusing. In one or more embodiments, the process includes a translational stage, a material reservoir, and a head and/or nozzle. The three-dimensional support member 70 when fabricated may comprise a substrate or base or stage portion. In one or more embodiments, the substrate or base or stage portion is cut and/or otherwise removed from the three-dimensional support member 70 prior to installation of the three-dimensional support member 70 in a subject. The substrate may be saved and/or stored. The substrate may be later utilized to form another three-dimensional support member 70 of a same or similar material. This substrate may further comprise a unique identifier for association with each customized three-dimensional support member 70. In one or more embodiments, the unique identifier is a unique combination of numbers and letters that is unique to each customized three-dimensional support member 70. An example of a unique identifier is one that includes: (i) six numbers representing the day that the support member was fabricated via the prototyping process (provided as two numbers only for the day, two numbers only for the month, and only the last two numbers of the year); and (ii) three letters representing the subject/patient for whom the support member was customized and fabricated for (provided as the first initial of the first name, the first initial of the middle name, and first initial of the last name).

Fabrication of the three-dimensional support member 70 may comprise, or may further comprise a tracking sheet, for capturing steps of the process, and/or for logging purposes, such as in a manufacturing process. For example, one or a plurality of steps of the process may be captured and/or logged, the steps comprising some or all of the following: (i) scanning and/or capturing in a plurality of images the hone/tissue and/or region thereof in need of a customized three-dimensional support member; (ii) obtaining on a computer volumetric data of the bone/tissue and/or region thereof from the scanned and/or captured images; (iii) preparing on a computer a rendering of the bone/tissue and/or region thereof in need of a customized three-dimensional support member; (iv) designing on a computer the customized three-dimensional support member by drawing/painting the customized three-dimensional support member on the computerized rendering of the bone/tissue and/or region thereof in need of a customized three-dimensional support member; (v) providing in an STL file or format the design of the customized three-dimensional support member; (vi) assigning in paper or on a computer associated with the design a unique identifier specific to the customized three-dimensional support member; (vii) reviewing the STL file or format for assurance and/or accuracy; (viii) loading the STL file or format onto a suitable three-dimensional printer; (ix) starting the printing of the customized three-dimensional support member based on the loaded STL file or format; (x) ending the printing upon completion; (xi) removing the printed three-dimensional support member and cut the printed three-dimensional support member from its stage and/or other removable substrate or structure(s); (xii) examining the printed three-dimensional support member e.g., against the STL file or format for assurance and/or accuracy); (xiii) salvaging and/or archive the cut stage and/or substrates; (xiv) undergoing post-processing of the printed three-dimensional support member (e.g., abrasive blasting, and/or sterilization); (xv) packaging and/or storing and/or shipping the printed three-dimensional support member (e.g., in a sterile container or pouch); (xvi) utilizing the printed three-dimensional support member (e.g., surgically installing in a subject or patient); (xvii) analyzing by a computer the design of the customized three-dimensional support member (e.g., utilizing the STL file or format in a modeling software program); (xviii) analyzing by an imaging device (e.g., CT scanner, MRI, ultrasound, etc.), the printed three-dimensional support member prior to and/or after utilizing the printed three-dimensional support member.

In one or more embodiments, the material used in the prototyping process forming the three-dimensional support member 70, is a metal. The metal may be a reactive metal. A suitable metal is titanium. Alternative metals, used alone or in combination with each other or with titanium, include but are not limited to titanium alloy, stainless steel, chrome, nickel based super alloy, cobalt, and gold, as representative examples. In some embodiments, the material may be a ceramic or ceramic composite. The material may also be a thermoplastic material (i.e., formed from a thermoplastic polymer or a polymer having thermoplastic properties or a polymer formed under thermoplastic conditions). In some embodiments, the material may be a thermoset material (i.e., formed from a thermoset polymer or a polymer having thermoset properties or a polymer formed under thermoset conditions). In some embodiments, the material may be a biologic material or a combination or biologic materials (e.g., cell, biologic polymer, protein, biologic chemical, such as calcium, etc.) used alone or in combination with other material(s) described above. Any of said materials may be used. Said material(s) must be biologically accepting materials (e.g., do not illicit a damaging or interfering immune reaction). The material may be provided in the prototyping or layering process in the form of a powder. The material may be provided in the prototyping or layering process in the form of a liquid. The prototyping or layering process provides the three-dimensional support member 70, which is duplicative of or embodied by the support construct 40 that was painted on the three-dimensional rendition 30.

In some embodiments, the three-dimensional support member 70 when formed serves as a prototype. In some embodiments, the three-dimensional support member 70 when formed serves as an actual device to be introduced in a patient in need thereof. In some embodiments, the three-dimensional support member 70 when formed serves as an implant to be introduced in a patient in need thereof. In some embodiments, the three-dimensional support member 70 when formed serves as a support structure for a tissue or a region thereof to be introduced at, in and/or around said tissue or region in a patient in need thereof. In some embodiments, the three-dimensional support member 70 when formed serves as an architectural framework for or replaces at least a part of the architecture of a tissue or a region thereof to be introduced at, in and/or around said tissue or region in a patient in need thereof. In some embodiments, the three-dimensional support member 70 when formed cooperates with the existing architectural framework of a tissue or a region thereof, and/or forms a replacement for at least part of the architectural framework of a tissue or region thereof, said three-dimensional support member co-existing and cooperating with said existing architectural framework, and/or in and/or around said existing architectural framework, in a patient in need thereof.

In any of the described embodiments, the three-dimensional support member 70 may or may not be further processed after being actively and initially fabricated by the prototype processing described above (in which the further processing may include one or more of milling, coating, surface treating, as representative examples, or some combination thereof).

The three-dimensional support member 70 fabricated by the prototyping process described above will, as described above, be duplicative of or will embody the painted support construct 40. Thus, taking the painted support construct 40 illustrated in FIG. 2A as an example, the three-dimensional support member 70 when processed via the prototyping action or steps (and prior to any final fabrication action or steps) will have the same general shape and size and configuration as the painted support construct 40 and will be composed of the material selected for the prototyping process.

Both the painted support construct 40 and the three-dimensional support member 70 formed therefrom will include one or more brace members 72 (as depicted with reference to painted support construct 40 of FIG. 2A), which may be further comprised of stress-distributing elements 74. The painted support construct 40 of FIG. 2A shows the three-dimensional support member 70 fabricated from the painted construct 40 having three spaced apart portions formed from brace members 72. Fewer or more brace member 72 are readily contemplated, depending on the tissue needs and extent of support and/or framework that is desired from the three-dimensional support member. In general, the one or more brace members 72 are, in operation, designed to cooperate with at least a portion of the tissue or region in need thereof, such that there are a plurality of contact locations along an opposing surface of the one or more brace members 72, which is the surface of the one or more brace members 72 that opposes and/or is in contact with and/or engages with the bone or tissue or region thereof that is exposed to the one or more brace members 72. In some embodiments, the plurality of contact locations provides a mating surface for the one or more brace members 72, such that the one or more brace members 72 follow the general surface architecture of the bone or tissue or region thereof that is exposed to the one or more brace members 72. In some embodiments, there are only a few contact locations although the one or more brace members 72 are still designed to follow the general surface architecture of the bone or tissue or region thereof that is exposed to the one or more brace members 72. In some embodiments, more than 50% of the opposing surface of the one or more brace members 72 has contact locations for mating with the exposed bone or tissue region. In some embodiments, less than 50% or less than 25% of the opposing surface of the one or more brace members 72 has contact locations for mating with the exposed bone or tissue region. In some embodiments, the exposed bone or tissue region on which substantially all the one or more brace members 72 will contact or engage with is an exterior surfaces of the bone or tissue region, said bone or tissue region having a normal, undamaged architecture. In some embodiments, the one or more brace members 72 will contact or engage with not only an exterior surfaces of the bone or tissue region (having its normal, undamaged architecture), the brace members 72 will also contact or engage with or oppose a damaged bone or tissue region or a bone or tissue region that requires repair, which may be on interior portion and/or an exterior portion of the bone or tissue region.

In some embodiments, the one or more brace members 72 are formed and designed to follow a general shape or surface architecture of the existing bone or tissue region. In some embodiments, the one or more brace members 72 are formed and designed to follow a general shape or surface architecture of the existing bone or tissue region as well as a proposed shape or proposed surface architecture, in which the proposed shape or surface architecture may be a shape or architecture prior to damage of the bone or tissue region (e.g., was the shape or architecture before the damage or loss of bone or tissue), or may be a preferred shape of the bone or tissue region (e.g., such as when undergoing a reconstruction and/or new construction of a bone or tissue region).

Often, when the one or more brace members 72 follow the general shape or surface architecture of the bone or tissue region and have few or limited contact locations with said exposed bone or tissue region, a filler material, described below, is provided to fill in the gap or distance between the one or more brace members 72 and the exposed bone or tissue region. Such a gap or distance between the bone exposed bone or tissue region and one or more brace members 72 is often found when the one or more brace members are positioned near a damaged portion of the bone or tissue region or a bone or tissue region to be repaired, in which the damaged portion represents a site of injury, damage, surgery, and/or disease and the bone or tissue region to be repaired represents an area that may be damaged or may be shaped to an alternative or preferred shape. Accordingly, in some embodiments, the three-dimensional support member 70 (and said one or more brace members 72) will have limited or little or no contact with said damaged portion of the bone or tissue region (e.g., the site of injury, damage, surgery, and/or disease) or limited or little or no contact with the bone or tissue region to be repaired, while having contact locations with bone or tissue regions neighboring the damaged portion of the bone or tissue region or the bone or tissue region to be repaired. The contact locations of the three-dimensional support member 70 (and said one or more brace members 72) at positions neighboring the damaged portion of the bone or tissue region (and/or the bone or tissue region to be repaired) while having limited or little or no contact with said damaged portion of the bone or tissue region (and/or the bone or tissue region to be repaired) allows the three-dimensional support member 70 to serve as a support or scaffolding, keeping the overall shape of the bone or tissue region in a preferred position (which is generally a position of the bone or tissue region prior to said damage, or may be a preferred position, such as one to be introduced during surgery). The one or more brace members 72 may assist in maintaining the bone or tissue in its preferred position. The one or more brace members 72 and/or the filler material may provide a further platform or network on which regeneration of new bone or tissue (remodeling and/or re-growth with new bone or tissue) may occur. Said further platform or network is often designed to be positioned directly near or adjacent damaged bone or tissue or the bone or tissue to be repaired. The combination of assisting in the support of the overall shape and/or position of the bone or tissue region and providing a further platform or network on which bone or tissue regeneration may occur is not found in many alternative devices. In some embodiments, the support portions of the three-dimensional support member may be designed to prevent or reduce bone or tissue regeneration. In some embodiments, the support portions of the three-dimensional support member 70 and/or the further platform or network may be designed to promote bone or tissue regeneration. The promotion of bone or tissue regeneration may be designed to be at site specific regions, such as by one or both of having a platform or network on which bone or tissue regeneration may occur and/or by including the filler material described below at site specific regions of the three-dimensional support member.

As described herein, the three-dimensional support member 70 will often have an overall configuration that complements the configuration (e.g., shape) of the exterior surface of the bone or tissue region along or for which the support member 70 is fitted, as depicted with respect to the painted support construct 40 of FIG. 2A. Additionally, in some embodiments, the three-dimensional support member 70 will include one or more platform or networks. The overall configuration is embodied by the one or more brace member 72 that follow the general exterior and/or exposed bone or tissue region configuration or architecture. For some bone or tissue configurations, the one or more brace members 72 may be designed on the painted support construct 40 to wrap fully or partially around, to fully or partially engulf, or to fully or partially encircle the bone or tissue region for which the final three-dimensional support member 70 is to be fitted for. This may be more common with many bone tissue, but may occur with any tissue for which the final three-dimensional support member 70 is to be fitted. The one or more brace members 72 and hence the three-dimensional support member 70 have a symmetric or non-symmetric configuration. For example, the overall shape or configuration of the three-dimensional support member 70 may be semi-circular (e.g., quarter circle, half-circle, etc.) or L-shaped or U-shaped, or V-shaped or any combination thereof. In some embodiments, the one or more brace members 72 and hence the three-dimensional support member 70 may so designed that it not only follows a general exterior or exposed architecture of the bone or tissue region but that is fittingly engages with at least a portion of the exterior and/or exposed architecture of the bone or tissue region. The fitting engagement will not only include contact locations it will prevent displacement of the three-dimensional support member 70, in which displacement is in at least one of an x, y or z direction, based on the x, y or z direction of the bone or tissue region. In one or more embodiments, the fitting engagement includes a lock-fit or a press-fit engagement of the three-dimensional support member with respect to the bone or tissue region to which it is fitted. Reinforcement for the fitting engagement may include stress-distributing elements 74, which join with each other and/or with the one or more brace members 72 at intersections 76. Stress distributing elements 74 are generally elongate and are spaced apart elements having gaps between said elements, so as not to form an overall (single) continuous solid mass. This prevents the three-dimensional support member 70 from becoming one continuous solid structure, and allows the one or more brace members 72 to form, instead, a network or meshwork or loose fabric-like structure that not only reduces the overall mass and amount of material required for any three-dimensional support member 70 when fabricated, it also allows for better ingrowth of new bone and tissue around and about the three-dimensional support member 70.

Figure 5:
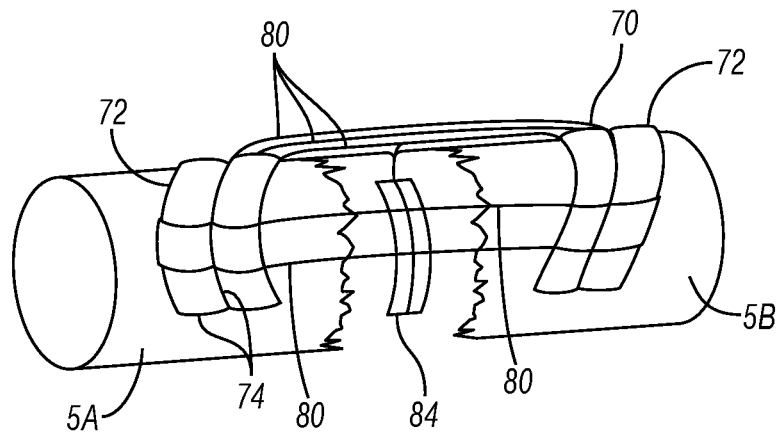
FIGS. 5 and 6 depict representative three-dimensional support members as described herein.

While the one or more brace members 72 will include a plurality of contact points or regions with the bone or tissue region (with respect to the exposed surfaces of the bone or tissue region), the contact points or regions may be spaced apart with respect to the exposed surface of the bone or tissue region, and said contact points or contact regions may be discontinuous. Thus, on the facing (opposing) surface of the three-dimensional support member 70, there will often be both contacting points or regions and areas that do not contact the bone or tissue region. Similarly, along any one stress-distributing element 74 there may be both contacting points or regions and areas that do not contact the exposed surface of the bone or tissue region. This is also illustrated in FIG. 5, as will be described below.

Figure 2B:
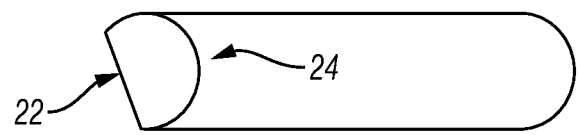
FIGS. 2B to 2I depict representative configurations for components of a support member as described herein.
Figure 2C:
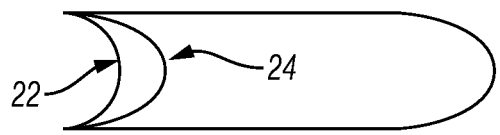
Figure 2D:
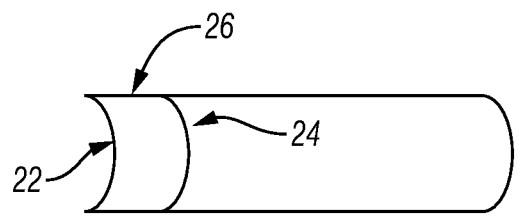

In one or more embodiments, the brace members 72, and the accompanying stress-distributing elements 74, have a hemispherical shape in cross section, as depicted in FIG. 2B. In one or more embodiments, the configuration of the brace members 72 and stress-distributing elements 74 will be similar, comprising a base portion 22, and at least an upper region 24. The base may also be semi-circular, as depicted in FIG. 2B or 2C. The upper region 24 may have planar sides 26, as depicted in FIG. 2C. Variations thereof are also contemplated. With such configurations, the base portion 22 will have contact regions for matingly engaging with or engaging within or contacting the bone or tissue. In some embodiments, the upper region and/or sides 26 may have a textured outer facing surface. In one or more embodiments, the base portion may have a length (end to end, in cross section) that is about 1.5 mm, or about 2.0 mm, or about 2.5 mm, or about 3.0 mm, or about 3.5 mm, or about 4.0 mm, or in any range there between or there about. For example, the base portion 22 of brace members 72 and stress-distributing elements 74 of FIGS. 2A, 7A and 7B are of a length of about 2.5 mm. In one or more embodiments, the height of the brace members 72, and of the stress-distributing elements 74 (e.g., from a center portion of a base to a peak height of an upper region 24, as depicted by "h" in FIG. 2B) is about 0.5 about mm, or about 1.0 mm, or about 1.5 nm, or about 2.0 mm, or about 2.5 mm, or in any range there between or there about. For example, the height of the brace members 72 and stress-distributing elements 74 of FIGS. 2A, 7A and 7B are about 1.0 mm.

Figures 2E, 2F, 2G:
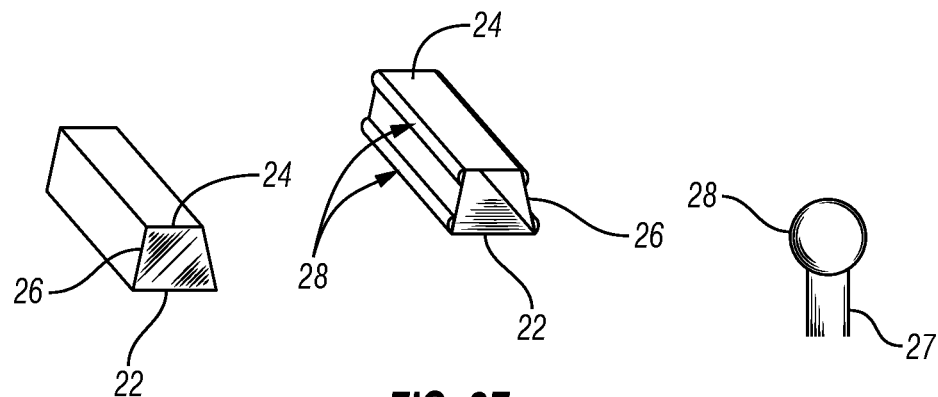

When formed, the three-dimensional support member 70, which includes a plurality of brace members 72, which comprise a plurality of stress-distributing elements 74 in a network, meshwork, or interlocking pattern, may have said brace members 72 in a spaced apart arrangement, as depicted with respect to the painted support construct 40 of FIG. 2A, which is utilized to form the three-dimensional support member 70. The spaced apart brace members 72 are united by at least one linking member 80. In some embodiments, the at least one linking member 80 is purposefully extended away from (elevated or raised some short distance from the bone or tissue region, of a sufficient distance in order to prevent contact with the bone or tissue region) and, thus, does not include any surface that is in contact with the exposed surface of the bone or tissue region, as is depicted in FIG. 2A. When linking member 80 is extended away from the bone or tissue region, the linking member may include extender 79 for displacing or extending the linking member in a manner that is sufficient to prevent contact of the linking member 80 with the bone or tissue region. In one or more embodiments, the linking member 80 embodies a strut of the support member device 70 and may help keep two (or more) tissue components (and/or accompanying spaced apart brace members) separate, and/or may help resist or minimize longitudinal compression (such as compression along a longitudinal length of the linking member 80). In one or more embodiments, all or a portion of the linking member 80 may have a shape, as depicted in one or both of FIGS. 2E and 2F, which may provide a thicker and stronger member, or portion of the member. When such a thicker shape is in only a portion of the linking member 80, it may be provided as a reinforcing section 81, and may be at regions of impact and/or of higher stress or strain, such as depicted, or that may be obtained from modeling of the bone or tissue region, which may be performed by three-dimensional modeling software known and/or utilized in the art. In one or more embodiments, the shapes depicted in FIGS. 2E and 2F, such as for one or more reinforcing section 81, are trapezoidal, having a base portion 22 and an upper region 24 and sides 26. In one or more embodiments, the base portion of such a trapezoidal shape will have a length that is greater than the base portion of the brace members 72 and the stress-distributing elements 74. In one or more embodiments, the base portion of such the trapezoidal shape may have a length (end to end, in cross section) that is about 2.0 mm, or about 2.5 mm, or about 3.0 mm, or about 3.5 mm, or about 4.0 mm, or about 4.0 mm, or in any range there between or there about. For example, the base portion 22 of the reinforcing sections 81 of FIGS. 2A, 7A and 7B is of a length of about 3.0 mm. In one or more embodiments, the height of the trapezoidal shape (and/or the reinforcing section 81) (e.g., from a center portion of a base to a peak height of an upper region 24) is about 2.0 mm, or about 2.5 mm, or about 3.0 mm, or about 3.5 mm, or about 4.0 mm, or about 4.0 mm, or in any range there between or there about. For example, the height of the reinforcing sections 81 of FIGS. 2A, 7A and 7B are about 3.0 mm. In one or more embodiments, the length (end to end, in cross section) of the upper region of the trapezoidal shape (and/or the reinforcing section 81) is about 1.0 mm, or about 1.5 mm, or about 2.0 mm, or about 2.5 mm, or about 3.0 mm, or about 3.5 mm, or in any range there between or there about. For example, the length of the upper region of the reinforcing sections 81 of FIGS. 2A, 7A and 7B are about 2.0 mm. In one or more embodiments, the trapezoidal shape may include one or more beaded edges 28, as depicted in FIG. 2F. The beaded edges 28 will increase the length of the base portion, when located on the edges of the base portion. The beaded edges 28 will increase the length of the upper region, when located on the edges of the upper region. By including beaded edges 28 on the edges of base portion 22 of FIG. 2F, the length of the base portion 22 (end to end, in cross section) may increase by about 0.5 mm, or by about 0.25 mm, or about 1.0 mm, or any range there between or there about. For example, the base portion of the reinforcing sections 81 of FIGS. 2A, 7A and 79, when including beaded portions 28 may increase to 3.5 mm, rather than being 3.0 mm. Similarly, by including beaded edges 28 on the edges of upper region 24 of FIG. 2F, the length of the upper region 24 (end to end, in cross section) may increase by about 0.5 mm, or by about 0.25 mm, or about 1.0 mm, or any range there between or there about. For example, the upper region of the reinforcing sections 81 of FIGS. 2A, 7A and 7B, when including beaded portions 28 may increase to 2.5 mm, rather than being 2.0 mm. In one or more embodiments, the trapezoidal shape (e.g., when formed as the reinforcing section 81) may have a longitudinal length, as depicted by "L" in FIG. 2E, may be about 4.0 mm, or about 4.5 mm, or about 5.0 mm, or about 5.5 mm, or about 6.0 mm, or about 6.5 mm, or about 7.0 mm, or in any range there between or there about. For example, a longitudinal length of the reinforcing sections 81 of FIGS. 2A, 7A and 7B is about 6.0 mm.

Figure 2H:
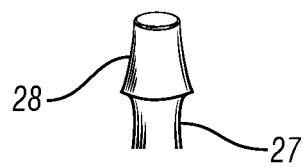
Figure 2I:
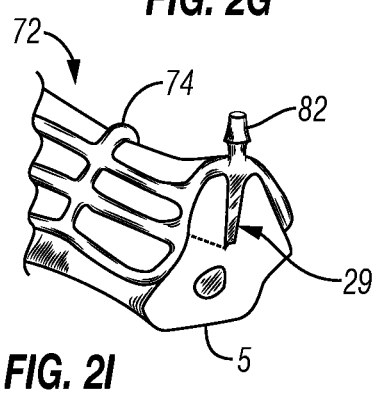

Additional features may be provided on the three-dimensional support member 70, such as one or more protrusions 82 for receiving an additional component or device. The one or more protrusions 82 typically extend from one or more brace members 72 and/or the at least one linking member 80. Examples of protrusions are depicted in FIGS. 2G and 2H. Looking at the configuration depicted in FIG. 2A, which is a rendition of a frame for receiving an addition device, the at least one linking member 80 is formed with protrusions 82, which are for removably receiving a denture. The additional features on the three-dimensional support member 70 may include bore holes, indentations, recesses, and other features. In one or more embodiments, an endosseous blade 29, as depicted in FIG. 21, is included for penetrating into the bone or tissue region 5. In one or more embodiments, one or a plurality of endosseous blades 29 may be positioned at or adjacent a protrusion, as depicted in FIG. 21. In other embodiments, one or more endosseous blades 29 may be provided along portion of the device that require reinforcement, and/or more precise positioning. In other embodiments, one or more endosseous blades 29 may be provided to prevent lateral movement of the three-dimensional support member 70. In some embodiments, the endosseous blade 29 will penetrate to a depth that does not interfere with blood supply and/or blood formation (e.g., does not penetrate a central cavity or canal or primary blood route). The endosseous blade 29 may have a length of the blade that is greater than a width, or the length and width of the blade may be similar.

In use, the three-dimensional support member 70 when formed from the painted support construct 40, such as depicted in FIG. 2A, is typically formed with some, or with many of the additional features. However, some of the additional features may be fabricated or installed in further processing steps, performed after fabrication of the three-dimensional support member 70, which is prepared by the prototyping process described above. When the three-dimensional support member 70 is fully formed and ready for use, such as in a subject or patient in need, the three-dimensional support member 70 is generally positioned so that at least portions of the one or more brace members 72 are in contact with the exposed surface of the bone or tissue region. The positioning will include fitting the three-dimensional support member 70 along the bone or tissue region having the compatible architectural features as those designed on the three-dimensional support member 70. The positioning may include guiding and/or press fitting or lock fitting so that the one or more architecturally compatible portions of the three-dimensional support member 70 are on and/or adjacent the bone or tissue region(s). It is also understood that positioning of the bone or tissue regions may include a repositioned of the bone or tissue region, such as in a preferred position (e.g., a position suitable for tissue healing, repair and/or remodeling), so that the bone or tissue region is configured to mate with the one or more architecturally compatible portions of the three-dimensional support member 70. The repositioning may likely include reintroduction of any separated tissue region(s) with as little gap or space there between. In some embodiments, however, some regions, when repositioned may still comprise one or more gaps there between (e.g., because of disease, loss of tissue, surgery, and/or fracture). With the positioning, or after the positioning, a filler material, as described below, may be provided. The filler material may also be provided before the positioning. The filler material may be distributed site specifically, such as along areas of the three-dimensional support member 70 that are amenable to new tissue growth, or along the entire length and/or width of the three-dimensional support member 70. In addition, or as an alternative, the filler material may be distributed in gaps that arise between the three-dimensional support member 70 and the exposed surface of the bone or tissue region.

FIG. 5 illustrates another representative three-dimensional support member 70 having two brace members 72 in a spaced apart arrangement. Said spaced apart brace members are united by a plurality of linking members 80. The embodiment of FIG. 5 serves as a support for two regions 5A and 5B of bone, in which the two regions are set apart. It is understood that this is merely representative on any type of tissue and any number of regions. The separation of the bone regions 5A and 5B may be a complete or partial separation and may have arisen from a fracture, non-union, surgery, or disease, as examples. The two regions 5A and 5B may not have resulted in a physical separation of the bone or tissue (e.g., such as from a hairline fracture). For example, regions 5A and 5B may be joined (not shown), or include portions of which remain joined (not shown). Thus, the illustration in FIG. 5 is merely representative to show certain described components.

In some embodiments, the three-dimensional support member 70 may further comprise an intervening segment 84, as depicted in FIG. 5. The intervening segment 84 may be configured to reside entirely between or partially between bone or tissue regions, such as between regions 5A and 5B of FIG. 5, and/or may include an architectural configuration compatible with an exposed surface of either or both regions 5A and 5B. The intervening segment 84, when present, may include one or more brace members 72 with or without stress-distributing elements 74. The intervening segment 84 may also be a solid element or may include some solid features (e.g., one or more plate regions) and one or more brace members. Solid or plate portions are typically included when bone or tissue growth is less desirable between the bone or tissue regions (that the intervening segment 84 is positioned between). One or more brace members are typically included when bone or tissue growth is desirable between the bone or tissue regions (that the intervening segment 84 is positioned between).

In FIG. 5, the three-dimensional support member 70 is shown with at least five linking members 80. The one or more linking members 80 unite the brace members 72 and the intervening segment on the same support member while allowing them to remain set apart from each other. Accordingly, the one or more linking member 80 keep the one or more brace members in its spaced apart arrangement. In the embodiment depicted in FIG. 5, the linking members 80 also traverse the gap formed between the two regions 5A and 5B. In addition the two brace members 72 are positioned and designed to be architecturally compatible with healthy tissue regions, supports and framing the healthy tissue regions while not interfering with or providing less direct contact with damaged or sensitive tissue (e.g., within the gap between the two regions 5A and 5B). In some embodiments, a filler material, as disclosed below, may be provided, such in areas between the three-dimensional support member 70 and healthy tissue (e.g., exposed outer surface of the bone or tissue regions) or in areas around or between the intervening segment 84, when the intervening segment 84 is included in or near a gap formed between the two regions 5A and 5B.

Figure 6:
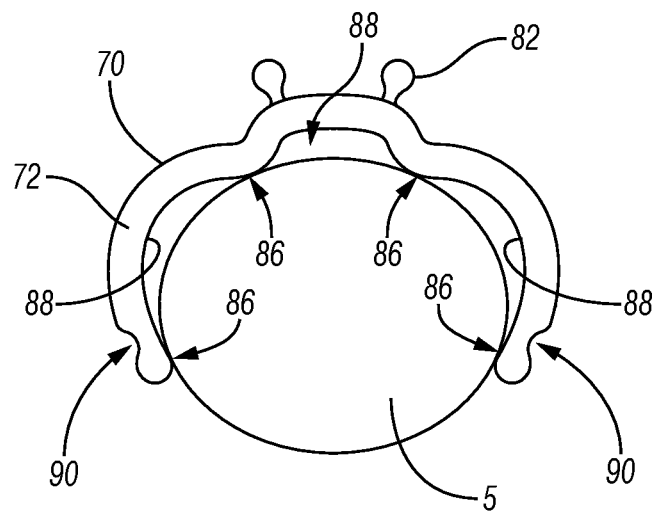

In FIG. 5, each brace member 72 is depicted as wrapping or encircling at least a portion of either region 5A or region 5B. This may not always be possible. Thus, not all brace members 72 may wrap around or at least partially encircle a bone or tissue region. Due to a non-uniform surface structure of region 5A and region 5B and/or due to a specific and/or desirable design configuration, there may be contacting surface regions and non-contacting surface regions between the facing surface side of brace members 72 and the exposed bone or tissue regions. A representative example of this is depicted in FIG. 6, showing a tissue 5 in cross-section, the tissue 5 having the three-dimensional support member 70 thereon. In FIG. 6, the three-dimensional support member 70 is purposefully designed to include at least one brace member 72 having contacting regions 86 and non-contacting regions 88. The three-dimensional support member 70 of FIG. 6 is further illustrated with projections 82 and bores 90, into which a screw or other component may be introduced. These additional features are optional. In FIG. 6, the brace member 72 is illustrated as having a similar architectural configuration as the exterior or exposed surface of the tissue 5 and fittingly engaging with the exterior or exposed surface of the tissue 5. The fitting engagement includes having the brace member 72 at least partially wrap around or encircle at least a portion of the tissue 5 in a manner that may form a lock-fit configuration.

In one or more embodiments described herein, the three-dimensional support member 70 when fully processed may serve as a frame to sit on or rest fittingly on a bone or tissue region. As a frame, the three-dimensional support member 70 may receive one or more additional components (e.g., receiving a denture when fitted on a mandible; receiving one or more screws and/or plates when fitted on bone; receiving an articulating element when fitted at an articulating position or joint).

The three-dimensional support member 70 when fully processed may be a prosthesis. The three-dimensional support member 70 when fully processed may be a stabilization device. The three-dimensional support member 70 when fully processed may be an implant. The three-dimensional support member 70 when fully processed may be intermediary filler or transitional device for new tissue in growth. The three-dimensional support member 70 when fully processed may be a weight-bearing support member, or a non-weight bearing support member, or combinations thereof. Any of the described uses of said three-dimensional support member 70 may be implemented alone or in combination.

In one embodiment, the three-dimensional support member 70 may include different and/or additional prototyping processes or a combination of further steps with the described prototyping processes that provides a three-dimensional support member 70 having different surface structures and/or surface characteristics, such as a roughened and/or abraded surface on some surface portions (e.g., portions in contact with or adjacent the bone or tissue region), a smooth surface on some surface portion (e.g., portions to which no biologic interaction is necessary or desired), a biologic-receiving surface on some surface portions (e.g., coated and/or porous portions to which biologic interaction is necessary or desired). As an example, a three-dimensional support member 70 when fully processed to be embody support construct 40 painted on the three-dimensional rendition 30 may include one or all of the following: (i) an upper surface that is smooth (for providing less tissue adhesion and/or in-growth); (ii) an upper surface that is textured and/or somewhat porous (having porosities therein) (for providing bone or tissue adhesion and/or bone or tissue in-growth); (iii) upper and/or lower surfaces or portions thereof with no contact points (based on no contact of the painted support structure 40 with the three-dimensional rendition 30); (iv) a lower surface that is roughened or textured and/or somewhat porous (having porosities therein) (for providing bone or tissue adhesion and/or bone or tissue in-growth); and/or (v) upper and/or lower surfaces or portions thereof with contact points (based on contact of the painted support structure 40 with the three-dimensional rendition 30). In one or more embodiments, smooth and texturing of the one or more surfaces may be provided by an abrasive blasting procedure or micro-abrasive blasting procedure, as is utilized and known in the art (e.g., utilizing an abrasive such as metal, sand, glass, and/or a chemical, as examples of the abrasive).

Figure 3A:
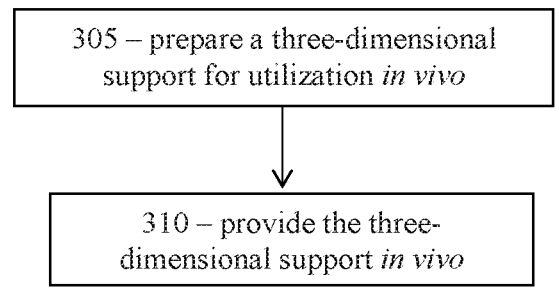
FIGS. 3A to 3C are representative methods as described herein of utilizing a support member as described herein.
Figure 3B:
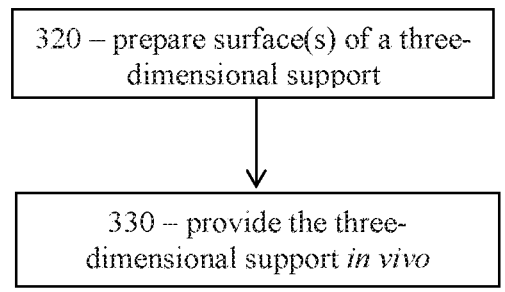

The three-dimensional support member 70 when fully processed may be utilized as depicted in FIG. 3A, 3B. 3C. In some embodiments, no intermediate fabrication is required. In some embodiments, no post processing steps to further modify the support structure are required. In some embodiments, no modifications of elements of the support structure are required. In some embodiments, no post analyses are required. In one or more embodiments, the three-dimensional support member 70 when fully processed by the prototyping process is ready for use. In some embodiments, the three-dimensional support member 70 when fully processed by the prototyping process is ready for use, and may simply be sterilized prior to integrating in or providing to a body requiring the support member. Thus, the design, fit and construction of the actual three-dimensional support member 70 is, in one or more embodiments, implemented entirely from the painted support construct 40 that was painted on the three-dimensional rendition 30. The three-dimensional rendition 30 being made from images obtained from the bone or tissue region as described previously, and the three-dimensional support member 70 being formed from data about the painted support construct 40, and thereby embodying the painted support construct 40 that was painted on the three-dimensional rendition 30. It is understood, however, that some additional fabrication, modifications, post processing steps, and/or post analyses may be implemented, which still provide a three-dimensional support member 70 implemented from the painted support construct 40 that was painted on the three-dimensional rendition 30. Accordingly, even with implementation of additional fabrication, modifications, post processing steps, and/or post analyses, the three-dimensional support member 70 is still derived directly from images obtained from the bone or tissue region, as described previously, and the three-dimensional support member 70 being formed from data about the painted support construct 40 still embodies the painted support construct 40 that was painted on the three-dimensional rendition 30.

FIG. 3A illustrates providing the three-dimensional support member 70 in vivo (block 310), in which the three-dimensional support 70 is delivered in vivo to the same tissue or bone region from which the three-dimensional rendition 30 was rendered and/or prepared. The three-dimensional support member 70 is introduced in vivo to the same tissue or bone region by any suitable means, including surgical placement, graft, etc. In one or more embodiments, the three-dimensional support member 70 is initially prepared prior to providing the support member 70 in vivo (block 305). For example, the support member 70 may be prepared by being sterilized utilizing an appropriate sterilization process understood and/or utilized in the art. A representative sterilization process may include cleaning, washing, passivation (e.g., with nitric acid), and drying. In addition, or as an alternative, the support structure 70 may be prepared by providing a unique identifier on the support member 70, and/or on a removable stage or base (e.g., a stage or base that is associated with the support member 70 during the additive manufacturing process, but is removable therefrom at some time after the additive manufacturing process and prior to introduction of the support member 70 to the bone and/or tissue region).

In a representative example, a mandible (previously extracted) was scanned using a cone CT imaging device. The images from the CT were captured and transferred to an .STL file set, set file set being housed on a server associated with a processor. The .STL file set when implemented by the processor or another computer depicted a rendition of the mandible on which a support construct was painted on the computer depicted rendition using appropriate software. The rendition and painted construct are depicted in FIG. 2A. The data files for the painted construct were used, implemented in an additive manufacturing process in the additive manufacturing process, a titanium powder was utilized. The powder may be pure titanium (e.g., Grade 1, such as one containing, consisting essentially of, or comprising, generally spherical particles of about 25 micrometer in diameter, or having (or containing, or consisting essentially of, or comprising), on average a diameter of about 25 micrometers, or having a range of diameters, from between about 5 micrometers to about 50 micrometers, of any size, or any range of sizes, or any average size, or any average range of sizes therein. The powder may also be a titanium alloy (e.g., Grade 5, such as one comprising about 90% titanium, with about 6% aluminum, 4% vanadium, less than 0.25% oxygen or oxide, and less than 0.25% iron). In one or more embodiments, the metal utilized in the additive manufacturing process, such as the metal comprising, containing, and/or consisting essentially of titanium, is certified, and suitable for manufacturing, such as under AS 91000, or ISO 9000. The metal may be of a medical grade or of a commercial grade. For support structures comprising, containing or consisting essentially of a metal, such as titanium, the additive manufacturing process utilized may be a direct digital manufacturing utilizing laser sintering or selective laser melting (for fine particle sizes of the size described herein). In some embodiments, electron beam melting is not preferred (for fine particle sizes of the size described herein). In some embodiments, prior to implementing the metal in the additive manufacturing process, the particles are sized appropriately, such as via a sieve or mesh. This action prevents larger particle sizes, or unwanted particle sizes. In some embodiments, such as when the particle sizes are to be about 25 micrometer in diameter, particles greater than 25 micrometer, and particles less than 25 micrometers are filtered (e.g., in accordance with ASTM B214-07). Such particles may be filtered to obtain a narrow size distribution. Such particle sizes may be tested by laser (e.g., testing in accordance with ASTM B822-10). Particles or lots thereof may be obtained by segregation and/or blending (e.g., in accordance with ASTM B215-10).

The titanium three-dimensional support frame when finished and fully fabricated by the described prototyping process, as depicted in FIGS. 7A and 7B, embodied the painted construct, and in these examples were created and constructed with brace members that were compatible with and conformed with the surface architecture of the mandible. In this example, the titanium three-dimensional support frame was a replica of the painted construct and fittingly engaged with the mandible in the same manner as shown in FIG. 2A. No post processing steps were implemented with production of the titanium three-dimensional support frame depicted in FIGS. 7A and 7B. Test samples of the three-dimensionally printed titanium described above, when tested for irritation and skin sensitization (ISO 10993-10, 2010), and for biological evaluation (ISO 10933-12, 2012) were found negative for irritation and skin sensitization when injected intracutaneously in rabbits, and were found negative for signs of toxicity, thereby meeting the requirements for ISO 10993-10 and ISO 10993-12 guidelines. Test samples of the three-dimensionally printed titanium, when tested for irritation and skin sensitization (ISO 10993-10, 2010), and for biological evaluation (ISO 10933-12, 2012) were found negative for irritation and skin sensitization when administered in vivo in guinea pigs, and were found negative for signs of toxicity, thereby meeting the requirements for ISO 10993-10 and ISO 10993-12 guidelines. Test samples of the three-dimensionally printed titanium, when tested for biologic reactivity (IS 10993-5, 2009) were found negative for biologic reactivity and negative for any cytotoxic effect when provided with mouse fibroblast CCL-1 cells (ATCC NCTC clone 929 or L929 cells) in culture, thereby meeting the requirements for ISO 10993-5 guidelines.

Figure 3C:
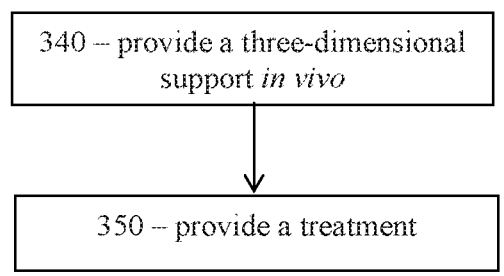

FIG. 3B illustrates preparing all or a portion of the surface of the three-dimensional support member 70 (block 330) before delivering in vivo the three-dimensional support member 70 (block 340) by any of the suitable means described with FIG. 3A, Again, the three-dimensional support member 70 is delivered in vivo to the bone or tissue region from which the three-dimensional rendition 30 was rendered. The preparing of all or portions of the surface of the three-dimensional support member 70 may include post-processing being implemented by a surface treatment, a coating, or the like provided to all or a portion of the facing surface of the three-dimensional support member 70 (e.g. after the three-dimensional support member 70 is fabricated by the prototyping process). The preparing of all or portions of the surface of the three-dimensional support member 70 may also be implemented during the prototype processing steps in which a surface treatment, a coating, or the like are provided during the additive manufacturing phase. In some embodiments, a filler material as a surface enhancer is provided to the three-dimensional support member 70. One example of a filler material is the filler material described below, which is a comingled blend of a stabilized blood product (e.g., autogenous platelet rich plasma, platelet rich fibrin), and a morphogenetic factor (sometimes or also referred to as morphogenetic protein, morphogenic factor, or morphogenic protein). When the tissue or tissue region is bone, a bone morphogenetic protein (BMP) may be comingled with the stabilized blood product, and provided as the surface enhancer. Or any other tissue morphogenetic protein (TMP), or a combination of such factors may be comingled with the stabilized blood product, and provided as the surface enhancer, FIG. 3C illustrates delivering in vivo the three-dimensional support member 70 (block 340) by the suitable means described with FIG. 3A followed by providing a treatment to all or a portion of the surface of the three-dimensional support member 70 (block 350). Again, the three-dimensional support member 70 is delivered in vivo to the bone or tissue region from which the three-dimensional rendition 30 was rendered. The providing the treatment may include a surface treatment provided to all or a portion of the surface after the three-dimensional support member 70 is delivered and positioned in vivo. The surface treatment may be the filler material described herein (e.g., a comingling of some stabilized blood product, as exemplified herein, and one or more growth factors, such as growth factors specific or suitable for the bone or tissue region for which the three-dimensional support member 70 was configured for). The providing the treatment may also include providing said filler material between the three-dimensional support member 70 and the exposed surface of the bone or tissue region after delivering in vivo the three-dimensional support member 70 to said bone or tissue region. The providing the treatment may also include providing the filler material to both the three-dimensional support member after its delivery in vivo and providing the treatment to exposed areas of the bone or tissue region or to near or neighboring areas of the bone or tissue region.

Thus, in one or more embodiments, the three-dimensional support member 70 is provided with an enriched environment before and/or after delivering the three-dimensional support member 70 in vivo. The surface enhancer described above may further comprise additional platelets, stem cells and/or growth factors, particularly stem cells pretreated to exhibit the morphology of the bone or tissue region to which it is delivered, or growth factors compatible with the bone or tissue region to which it is delivered. The additional stem cells and/or growth factors may also be obtained from the subject or patient to which the three-dimensional support member is to be delivered to.

Figure 4A:
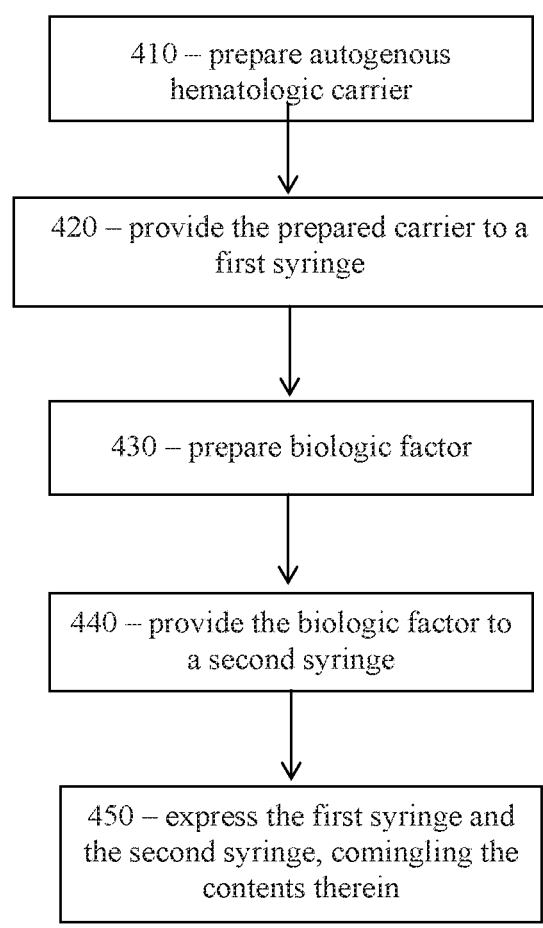
FIGS. 4A and 4B are representative methods of preparing an enhancer as described herein.
Figure 4B:
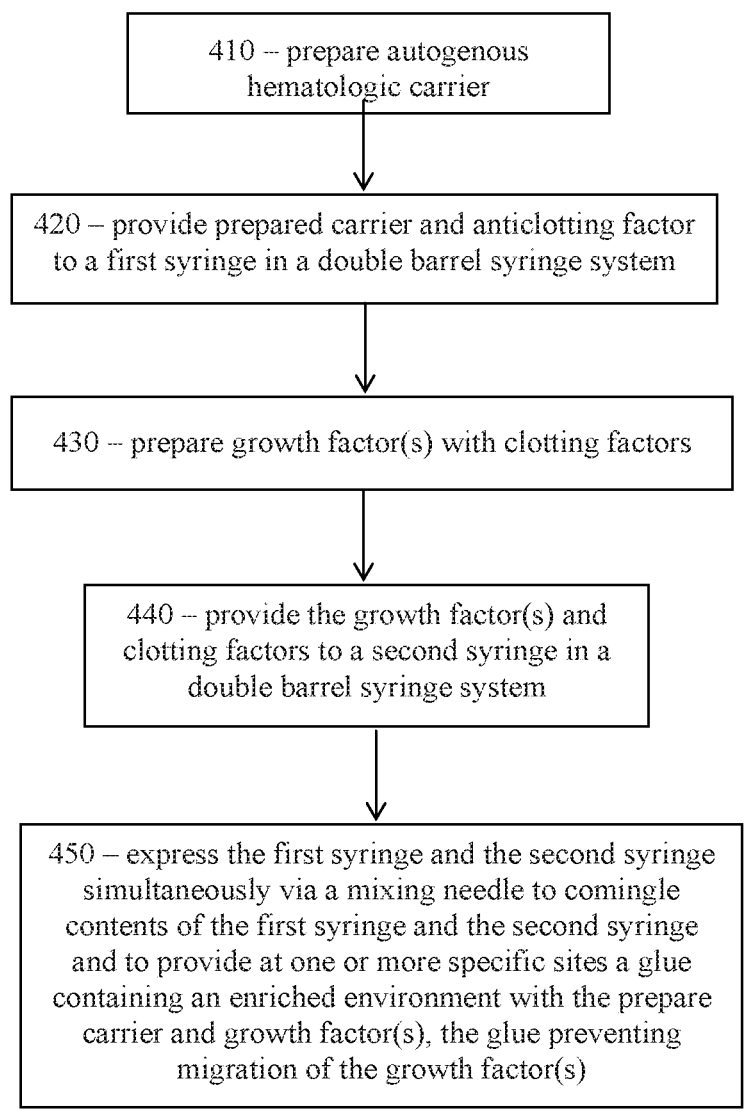

Representative methods of preparing the filler material, which may be provided as a surface enhancer described above, are depicted in FIGS. 4A and 4B. In these examples, the filler material includes one or more growth factors, and an autogenous hematologic carrier. The growth factor is a protein or hormone. The growth factor may be a morphogenetic factor. The growth factor may be or include a BMP, such as BMP-2, BMP-7. The growth factor and/or the morphogenetic factor may be specific for tissue or tissue region. The growth factor and/or the morphogenetic factor morphogenetic factor may be tailored and/or specific for a desired cell type or cell genotype. The growth factor and/or the morphogenetic factor morphogenetic factor may be in a recombinant form. The growth factor and/or the morphogenetic factor may be in a human recombinant form. Any form suitable for introduction to a subject or patient (e.g., with delivery of the three-dimensional support member 70) may be utilized. The autogenous hematologic carrier is a stabilized blood product (e.g., autogenous platelet rich plasma (PRP), platelet rich fibrin (PRF)). The autogenous hematologic carrier is an improved environment for delivering the one or more growth factors to the three-dimensional support member 70 (and/or regions neighboring the support member) when introduced by the means described with FIG. 3A. The filler material serves to assist and/or initiate endogenous bone or tissue generation, the bone or tissue generation occurring after introduction of the three-dimensional support member 70 and the filler material.

Referring again to FIGS. 4A and 4B, the surface enhancer may be introduced by initially preparing the autogenous hematologic carrier as a stabilized blood product, which is obtained from the same individual (block 410) using known methods of preparing such products. For example, plasma obtained from said individual is mixed with an anti-clotting chemical, centrifuged to specifically isolate in particular fractions the platelets, stem cells and growth factors from said individual, to obtain a concentrated mixture of autogenous stem cells, autogenous platelets, autogenous growth factors and autogenous cytokines at a concentration much greater than found in blood plasma (volume to volume). The concentrated mixture may be used upon centrifuging and concentrating (e.g., as PRP), or may be or further supplemented with additional harvested stem cells or pluripotent cells (that may or may not be from the same individual), or supplemented with a fibrin matrix, such as one polymerized in a tetra molecular structure (e.g., as PRF), in which the fibrin matrix in the tetra molecular structure incorporates the concentrated blood collection (comprising the platelets, leucocytes, cytokines, and circulating stein cells). These so-obtained concentrate (autogenous hematologic carrier as a stabilized blood product) may also be mixed with an additional amount of the anticlotting chemical. The so-obtained autogenous hematologic carrier (with or without additional supplements or anti-cloning chemical(s)) is provided as a first composition in a first syringe (which may be a first syringe of a double barrel syringe) (block 420). A second composition is prepared, which is the growth factor (block 430). The growth factor may be from the same individual. The growth factor may be prepared by alternative methods. In one or more embodiments, the growth factor is a recombinant human (rh) growth factor, such as rhBMP-2. In some embodiments, the growth factor is supplemented with a clotting factor (e.g., thrombin with or without calcium chloride). In one or more embodiments, the growth factor is supplemented with even further additional components, such as cells, further growth factors and/or activators, including but not limited to one or more differentiating cells and/or one or more morphogenetic proteins, acting, e.g., as triggers, initiators, or catalysts. In one or more embodiments, the growth factor is supplemented with other materials that may serve as scaffolding, such as components for forming a calcium-based matrix, or components from autogenous bone, or other autogenous tissue. The growth factor is provided to the second syringe (which may be a second syringe of a double barrel syringe) (block 440). Any alternative system may be used to introduce the two compositions. Preferably said first and second compositions remain separate until introduced, to cormingle, or remain separate until just prior to use. The first and second compositions may be introduced to the three-dimensional support member 70 prior to introducing the three-dimensional support member 70 in vivo, to the subject or patient at or near the bone or tissue region in vivo (e.g., localized at or around the site the three-dimensional support member 70 is to be introduced), and/or to the three-dimensional support 70 after the three-dimensional support member 70 is introduced in vivo.

In some embodiments, with use of a double barrel syringe, plungers of the first and second syringes are joined so that both plungers advance at the same rate. In some embodiments, with use of a double barrel syringe, the first composition and the second composition are expressed simultaneously from each syringe. In some embodiments, such as with use of a double barrel syringe, the contents of one syringe is expressed in advance of contents of the other syringe. When simultaneously expressed, a mixing needle may to used, at which point the first and the second compositions are comingled and may be intermixed. As contents of the two syringes are comingled (either in vivo, or in the mixing needle), nearly immediate clotting of the contents will occur. The combination of the first and the second composition provides a glue substance when introduced and co-combined and, in some embodiments, will clot. This biologic glue may be delivered site specifically and, with clotting, will remain without substantially dispersing, which without said glue could lead to growth in unintended regions. The biologic glue is utilized to physiologically affix components of the first and/or second composition to the individual bone or tissue region (said bone or tissue region having been utilized to make the three-dimensional support 70 and to which the three-dimensional support 70 is delivered). The biologic glue provides an enriched biologic environment for growth of the bone or tissue region once or after the three-dimensional support 70 in combination with the biologic glue are introduced in vivo. The first and second compositions are often designed as a biologic glue for the bone or tissue region to which it is to be introduced. It has been found that a three-dimensional support 70 constructed in the manner described herein and introduced, with addition of the biologic glue described herein, provides endosseous bone growth when the three-dimensional support 70 and the biologic glue were introduced to a bone region.

The completely customized support structures described herein do not require any initial fitting to the actual tissue for which the support structure is configured for, and thereby none of the support structures described herein require a debriding, and/or degloving of the tissue for manufacturing purposes. The completely customized support structures described herein do not require making an impression of the actual tissue in order to configure the support structure, thereby the support structures described herein does not require an intact tissue structure, nor any debriding, and/or degloving of the tissue for implementing the configuration of the structure. The completely customized support structures are directly configured to form a required shape (e.g., shape of a tissue) via non-invasive means, and therefore, none of the support structures require invasive steps to be taken for configuration and/or manufacturing of the support structure. None of the completely customized support structures are manufactured by extruding and/or forming the structure into a mold, requiring the mold to prepared first, often by initially fitting and/or computer modeling the mold, rather than the support structure. The completely customized support structures described herein reduce surgical time, reduce post-operative issues, reduce processing steps, and, thereby reduce the overall cost associated with manufacturing and/or providing the customized support structure for a subject or patient in need thereof.

The completely customized support structures described herein are customized for a tissue, such as bone, of a subject/patient, such as a subject or patient in need thereof. Each customized support structure is configured to fit and/or complement specific anatomy of the tissue, including anatomy neighboring and/or adjacent a tissue region for which the customized support structure is configured for. In one or more embodiments, fit of a customized support structure has a high accuracy in relation to the tissue region for which it complements and/or fits, and any difference in fit may be in the micrometer range. In some embodiments, any different in fit and/or accuracy between the structure of the tissue for which the customized support is configured for, and the structure of the actual customized support that is fabricated, is less than 100 micrometers, or is less than 50 micrometers.

Each customized support structures described herein is fabricated from a three-dimensional embodiment or representation of the anatomy for which that customized support structure is configured for. The three-dimensional embodiment are obtained from actual images of the tissue, and/or may include overlays (from a suitable matching tissue) when a region of the tissue is absent. The three-dimensional embodiment or representation of the anatomy for which that customized support structure is configured for are obtained non-invasively. Similarly, the three-dimensional customized support structure may be fabricated without requiring any invasive measures to be taken prior to fabrication. In one or more embodiments, design and fabrication of the three-dimensional customized support structure may be performed in a manufacturing facility, in order to comply with material and/or safety requirements.

The customized three-dimensional support structure, once fabricated, may be tested prior to use (e.g., via computer modeling, and/or lab testing of, e.g., stress, strain, structural and/or biologic longevity and/or endurance, etc.).

The computer as described herein may be any computing device having one or more processors, and associated computer readable program codes. In one or more embodiments, what is embodied may include only software (e.g., data processing, computer program product, etc.). In one or more embodiments, what is embodied may include software, and hardware for design and fabrication of the three-dimensional support structure. Computer data for design and fabrication of the three-dimensional support structure may be digital data, collected, recorded and/or stored in the computing device and/or associated storage device, which may or may not be the same storage device storing the requisite software, and may or may not be the same storage device storing information and/or data about the support structure, and/or about the subject or patient (e.g., patient records). Any of the requisite data for design and fabrication as described herein may also be processed and/or accessed by one or more computing devices, in which suitable computing devices may include the type having a central processing unit comprising logic, control circuitry, and memory (e.g., as volatile memory, cache memory) in addition to a storage space or memory (e.g., as non-volatile memory). The computing device may be any form (e.g., desktop computer form, portable computing form, smartphone, personal computer, laptop, electronic tablet device, global positioning system (GPS) receiver, portable media player, personal digital assistant (PDAs), and/or network access device), including any processing device capable of receiving and transmitting data. At least one of the computing devices will require or will be coupled to a display screen. The display screen may preferably be a touch screen. A user should be able to interface with at least the at least one computing device. For example, for designing and/or painting as described herein, at least one device will have a display having or associated with a touch screen interface using, for example capacitive, resistive, or surface acoustic wave (also referred to as dispersive signal) touch screen technologies, or any other suitable technology for sensing physical interaction with the display, and for allowing manipulation of digital data, a digital model, and/or rendition, as described herein.

Data, including data for design and fabrication as described herein, may be recorded and/or stored on computer (machine) readable medium, in a computer (machine) readable form. A computer-readable medium may include any medium that participates in providing instructions to one or more processors of the computing device or controller for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or certain RAM. Transmission media may include coaxial cables, copper wire, fiber optic lines, and wires arranged in a bus. Transmission media may also take the form of electromagnetic, radio frequency, acoustic, or light waves, such as those generated during data communications, such as radio wave, and/or infrared data communications. The software associated with the design and/or fabrication, as described herein, is stored on the computing device in memory (e.g., RAM and/or cache memory), and/or on one or more alternative storage units (e.g., hard disk, magnetic disk, tape, or CD-ROM, one or more servers) and accessible by the computing device. As a further example, software may be accessible and/or transmitted via wires, radio waves, cloud computing (e.g., SaaS, PaaS, IaaS), and/or through a network such as the Internet. In operation, a system described herein may include one or more computer devices used to execute the software accessible by and/or associated with the one or more computing devices, which will be involved in implementing one or more of the embodiments and/or steps of the embodiments for the design and/or fabrication of the customized three-dimensional support structure described herein. One or more servers may also be associated with the one or more computing devices that are associated with for the design and/or fabrication of the customized three-dimensional support structure described herein. The one or more servers may include a client system operably coupled with and/or in communication with a network (e.g., via an access provider, and/or a server system). The client system(s) typically request information from the server system, which provides the information. In some embodiments, a computer system may act as both a client system and a server system depending on whether the computer system is requesting or providing information, and/or may act as a stand-alone computer system.

In one or more methods, and/or systems described herein, communication between the computer device and the image capture device (e.g., scanner) may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. The transmission may be secured. The computing device may generate control signals to the image capture device, which, in addition to image acquisition commands, may include conventional device controls. The computing device may include a network communications interface for connecting to and communicating with a network, such as a medical network, a manufacturing network, a distributing network, a patient network, and the like. The network may include one or more local area networks ("LANs"), which may remain local, or may be an interconnection of one or more computing devices through a hub (in, for example, a peer network such as a wired or wireless Ethernet network), or a local area network server (in, for example, a client-server network). The LAN may be connected through a gateway, which provides security to the LAN, and ensures operating compatibility between the LAN and the network. Any data network may be used as the network and the LAN.

The computing device may acquire a two-dimensional image or a set thereof of the tissue (for which a three-dimensional support device is to be configured for) at a specific rate, and/or at a specific time, which may be while the image capture device is operating, or after operation is complete. The two-dimensional image sets may be forwarded to the same computing device or a different computing device for derivation of volumetric data set (e.g., provided as three-dimensional point clouds). The volumetric data set for each two-dimensional image set may be derived and fitted or "stitched" to existing three-dimensional data using a number of different techniques known and/or utilized in the art, such as when a portion of the tissue is absent and/or defective. In some embodiments, the image capture system may be adapted for real time acquisition and display, e.g., at a video rate, of three-dimensional data, which may be rendered, for example, as a point cloud superimposed on a video image from the scanner. For certain types of data acquisition, there may be a significant difference in the processing time required for resolution of a three-dimensional image adequate for two-dimensional perspective rendering (faster) and maximum or optimum resolution that might be achieved with post-processing. In such circumstances, the image capture system may include two different operating modes. In a first operating mode, a relatively low-quality three-dimensional representation may be obtained and rendered in real time, such as within the display. In a second operating mode, a relatively high-quality three-dimensional representation may be generated for the source scan data using any desired degree of processing. The second operating mode may recover, through additional post-processing steps, three-dimensional data having greater spatial resolution and/or accuracy. It will be understood that, while two different modes are described, it is not required that the two modes be mutually exclusive. For example, both modes may execute simultaneously on a computer as separate processes or threads, or the data from the first operating mode may be employed to seed the second operating mode with a model for refinement for post-processing. All such variations as would be apparent to one of ordinary skill in the art may be employed with the systems described herein. In one or more embodiments, a high-quality representation, or both a high and low quality representation, may be transmitted to the computing device that will be utilized to design and/or paint as described herein.

The same or different computing device may direct or control the three-dimensional printing of the three-dimensional support utilizing a 3D printer. This computing device may comprise a central processing device, viewing interface (e.g., display monitor or screen), one or more input devices (e.g., keyboard and mouse), and software for at least instructing the 3D printer, and/or for operating with a computer-aided design ("CAD"), three-dimensional mapping, or other representation of the desired three-dimensional support providing as the painted support construct 40 (e.g., as a three dimensional pattern or image comprising data). This computing device may also include one or more second nontransitory computer-readable media encoded with a second computer program product loadable into a memory of the computing device or the 3D printer, as examples, and include second software code portions for instructing the 3D printer to print, through a sequence of printing steps, such the three-dimensional support is printed from or in association with data associated with the painted support construct 40. The 3D printer may require its own computing device for implementation of printing. The three-dimensional support when formed is dimensioned from information from images gathered about the tissue for which the support is configured for. The three-dimensional support itself when formed may take into account and be configured to include the three-dimensional surface irregularities and asymmetries that may be present on the tissue for which the support is configured for.

The present disclosure includes preferred or illustrative embodiments in which specific devices and methods are described. Other aspects and advantages may be obtained from a study of this disclosure and the drawings, along with the appended claims.

What is claimed is:

1. A tissue device fabricated by an additive manufacturing process comprising:
   one or more spaced apart brace members, and
   at least one elongated linking member for linking to the one or more spaced apart brace members,
   the tissue device further comprising in use a biologic glue, the biologic glue comprising:
      a first portion containing a stabilized blood product, and
      a second portion containing a growth factor, the first and second portions being comingled only when the tissue device is adapted for a subject in need thereof,
   wherein the stabilized blood product is any stabilized blood product, wherein the stabilized blood product may be or may include an autogenous stabilized blood product, and
   wherein the growth factor may be or may include any one or more of a tissue-specific growth factor, a cell differentiating factor, a tissue differentiating factor, and a tissue morphogenetic factor.

2. The tissue device of claim 1, wherein the first portion further comprises a supplemental agent.

3. The tissue device of claim 1, wherein the stabilized blood product is or includes any one or more of a platelet rich plasma, platelet rich fibrin, and fibrin rich plasma.

4. The tissue device of claim 1, wherein the second portion further comprises any one or more of a calcium chloride, thrombin, and one or more clotting factors.

5. The tissue device of claim 1, wherein the growth factor is selected from any one or more of a human growth factor, a human recombinant bone morphogenetic protein (BMP), a human recombinant BMP 2, a human recombinant BMP 7, a cell differentiating factor, and a morphogenic factor, wherein the cell differentiating factor and the morphogenic factor may be any one of autogenous, harvested, and manufactured.

6. The tissue device of claim 1, wherein at least some of the one or more spaced apart brace members provide a shape for the tissue device that is configured to complement a surface anatomy of tissue for which the tissue device is configured for, and at least some of the one or more spaced apart brace members are configured to be proximate or in intimate contact with the tissue for which the tissue device is configured for.

7. The tissue device of claim 1 further comprising any one or more of: (i) one or more projections; (ii) and one or more bore holes.

8. The tissue device of claim 1, wherein each spaced apart brace member includes at least one or more of: (i) a plurality of stress-distributing elements or struts, each spaced apart and interlinked in a manner so as to form at least one of a plurality of gaps, spaces, and openings therebetween, for ingrowth; and (ii) a networked arrangement that is not arranged as one continuous solid structure, and is, instead, configured to complement an anatomic surface shape of a tissue for which the tissue device is configured for.

9. The tissue device of claim 1, further comprising a plurality of stress-distributing elements provided with each of the one or more spaced apart brace members, wherein the plurality of stress-distributing elements provided with each of the one or more spaced apart brace members have an overall arrangement that is at least one of porous, an open pore pattern, and a mesh configuration.

10. The tissue device of claim 1, wherein the one or more spaced apart brace members is adapted to include at least one or more of: (i) a configuration that is complementary to and is adapted to a surface anatomy of a tissue for which the tissue device is adapted for, and is further configured to be proximate with at least some of the surface anatomy; and (ii) one or more contacting regions and one or more non-contacting regions, wherein the one or more contacting regions and one or more non-contacting regions are adapted to associate with at least a portion of the surface anatomy of the tissue for which the tissue device is adapted.

11. The tissue device of claim 1, wherein the at least one elongated linking member is not configured to contact tissue when the tissue device is positioned on a region of the tissue of the subject in need thereof for which the tissue device is adapted.

12. A system for providing a tissue device configured to complement at least a portion of a tissue, the system comprising:
a tissue device; and
a biologic glue,
the tissue device having one or more spaced apart brace members and at least one elongated linking member for linking the one or more spaced apart brace members,
wherein the tissue device forms any one of a mesh structure, a network, and a multiporous sheet structure, such that at least a portion of the tissue device is configured to complement at least a portion of an anatomic surface of the portion of the tissue for which the tissue device is configured for, and the tissue device is fabricated by an additive manufacturing process,
wherein the tissue device is adapted for support, reconstruction, or enhancement of the portion of the tissue,
wherein the biologic glue comprises at least a first portion containing a stabilized blood product, and a second portion containing a tissue specific growth factor, the first and second portions being separate until at or near a time that the tissue device or at least a portion of the tissue device is configured to be proximate to the tissue, and
wherein the tissue specific growth factor includes at least one or more of a morphogenetic protein, a growth factor, and a cell differentiating factor, the tissue specific growth factor being any one of harvested or manufactured.

13. The system of claim 12, wherein the tissue is adapted for any one or more of tissue regeneration, tissue reconstruction, anatomical enhancement, anatomic reconstruction, and tissue replacement, in which no further tissue or mechanical device is necessary, and when so adapted,
the tissue device is configured as at least one or more of tissue replacement framework, tissue reconstruction device, and integrated prosthesis.

14. The system of claim 12, wherein the tissue is a mandible, and the tissue device is configured to complement at least a portion of an exposed surface of the mandible, and wherein the tissue device is further configured as a frame to receive all or a portion of a denture.

15. The system of claim 12, wherein the tissue device is an intermediary device designed to assist in growth of new tissue.

16. The system of claim 12, wherein the tissue device is configured as an implant.

17. The system of claim 12, wherein the stabilized blood product is or includes any one or more of a platelet rich plasma, platelet rich fibrin, and fibrin rich plasma.

18. The system of claim 12, wherein the tissue device further comprises one or more of: (i) a plurality of stress-distributing elements associated with each of the one or more spaced apart brace members giving an overall porous or open pore pattern to the tissue device; (ii) one or more projections; and (iii) one or more bore holes.

19. The system of claim 12, wherein the second portion further comprises any one or more of a calcium chloride, thrombin, and one or more clotting factors.

20. The system of claim 12, wherein the growth factor is selected from any one or more of a human growth factor, a recombinant growth factor, a human recombinant bone morphogenetic protein (BMP), a human recombinant BMP 2, and a human recombinant BMP 7.

* * * * *